United States Patent
Masel

(10) Patent No.: US 10,975,480 B2
(45) Date of Patent: *Apr. 13, 2021

(54) ELECTROCATALYTIC PROCESS FOR CARBON DIOXIDE CONVERSION

(71) Applicant: Dioxide Materials, Inc., Boca Raton, FL (US)

(72) Inventor: Richard I. Masel, Boca Raton, FL (US)

(73) Assignee: Dioxide Materials, Inc., Boca Raton, FL (US)

(*) Notice: Subject to any disclaimer, the term of this patent is extended or adjusted under 35 U.S.C. 154(b) by 318 days.

This patent is subject to a terminal disclaimer.

(21) Appl. No.: 16/238,425

(22) Filed: Jan. 2, 2019

(65) Prior Publication Data
US 2019/0211463 A1   Jul. 11, 2019

Related U.S. Application Data

(63) Continuation-in-part of application No. 15/724,933, filed on Oct. 4, 2017, now Pat. No. 10,173,169, and
(Continued)

(51) Int. Cl.
*B01J 37/34* (2006.01)
*C25B 9/40* (2021.01)
(Continued)

(52) U.S. Cl.
CPC ............ *C25B 9/40* (2021.01); *C01B 32/40* (2017.08); *C07C 1/12* (2013.01); *C25B 1/00* (2013.01);
(Continued)

(58) Field of Classification Search
USPC ............................ 502/100, 150, 300
See application file for complete search history.

(56) References Cited

U.S. PATENT DOCUMENTS

| 1,919,850 A | 7/1922 | Luscher |
| 2,511,198 A | 6/1950 | Engel |

(Continued)

FOREIGN PATENT DOCUMENTS

| CA | 1272180 A | 7/1990 |
| CA | 2749136 A1 | 8/2010 |

(Continued)

OTHER PUBLICATIONS

U.S. Appl. No. 15/810,106, Office Action dated Feb. 6, 2020 ("20200206USOA"), Notice of Allowance May 26, 2020 ("20200526NOA").

(Continued)

*Primary Examiner* — James E McDonough
(74) *Attorney, Agent, or Firm* — Cook Alex Ltd.

(57) ABSTRACT

An electrocatalytic device for carbon dioxide conversion includes an electrochemical stack comprising a series of cells with a cathode with a Catalytically Active Element metal in the form of supported or unsupported particles or flakes with an average size between 0.6 nm and 100 nm. The reaction products comprise at least one of CO, $HCO^-$, $H_2CO$, $(HCOO)^-$, HCOOH, $CH_3OH$, $CH_4$, $C_2H_4$, $CH_3CH_2OH$, $CH_3COO^-$, $CH_3COOH$, $C_2H_6$, $(COOH)_2$, $(COO^-)_2$, and $CF_3COOH$.

18 Claims, 6 Drawing Sheets

Related U.S. Application Data a continuation-in-part of application No. PCT/US2015/014328, filed on Feb. 3, 2015.

(51) Int. Cl.

| | | |
|---|---|---|
| *C25B 13/08* | (2006.01) | |
| *C25B 1/00* | (2021.01) | |
| *C25B 15/08* | (2006.01) | |
| *C25B 11/04* | (2021.01) | |
| *C07C 1/12* | (2006.01) | |
| *C01B 32/40* | (2017.01) | |
| *C25B 3/25* | (2021.01) | |
| *C25B 9/23* | (2021.01) | |
| *B01J 21/00* | (2006.01) | |
| *B01J 23/00* | (2006.01) | |
| *B01J 25/00* | (2006.01) | |
| *B01J 29/00* | (2006.01) | |
| *B01J 31/00* | (2006.01) | |

(52) U.S. Cl.
CPC .............. *C25B 3/25* (2021.01); *C25B 9/23* (2021.01); *C25B 11/04* (2013.01); *C25B 13/08* (2013.01); *C25B 15/08* (2013.01)

(56) References Cited

U.S. PATENT DOCUMENTS

| | | |
|---|---|---|
| 2,996,359 A | 8/1961 | Mossman et al. |
| 3,779,883 A | 12/1973 | Heit |
| 3,896,015 A | 7/1975 | McRae |
| 3,959,094 A | 5/1976 | Steinberg |
| 4,240,882 A | 12/1980 | Ang et al. |
| 4,315,753 A | 2/1982 | Bruckenstein et al. |
| 4,456,521 A | 6/1984 | Solomon et al. |
| 4,474,648 A | 10/1984 | Tantram et al. |
| 4,474,652 A | 10/1984 | Brown et al. |
| 4,523,981 A | 6/1985 | Ang et al. |
| 4,545,872 A | 10/1985 | Sammells et al. |
| 4,595,465 A | 6/1986 | Ang et al. |
| 4,608,132 A | 8/1986 | Sammells |
| 4,608,133 A | 8/1986 | Morduchowitz et al. |
| 4,609,440 A | 9/1986 | Frese et al. |
| 4,609,441 A | 9/1986 | Frese et al. |
| 4,620,906 A | 11/1986 | Ang |
| 4,668,349 A | 5/1987 | Cueller et al. |
| 4,673,473 A | 6/1987 | Ang et al. |
| 4,701,437 A | 10/1987 | Boxhoorn et al. |
| 4,756,807 A | 7/1988 | Meyer et al. |
| 4,771,708 A | 9/1988 | Douglass, Jr. |
| 4,789,442 A | 12/1988 | Nakagawa et al. |
| 4,818,353 A | 4/1989 | Langer et al. |
| 4,879,070 A | 11/1989 | Kent |
| 4,921,585 A | 5/1990 | Molter |
| 4,968,393 A | 11/1990 | Mazur et al. |
| 5,064,733 A | 11/1991 | Krist et al. |
| 5,071,526 A | 12/1991 | Pletcher et al. |
| 5,089,661 A | 2/1992 | Maspero et al. |
| 5,206,433 A | 4/1993 | Hohenschutz et al. |
| 5,284,563 A | 2/1994 | Fujihara et al. |
| 5,294,740 A | 3/1994 | Kiefer et al. |
| 5,334,759 A | 8/1994 | Lippert et al. |
| 5,362,367 A | 11/1994 | Dapperheld et al. |
| 5,382,332 A | 1/1995 | Fujihara et al. |
| 5,639,910 A | 6/1997 | Ikariya et al. |
| 5,667,653 A | 9/1997 | Schneider et al. |
| 5,709,789 A | 1/1998 | Shay et al. |
| 5,763,622 A | 6/1998 | Podszun et al. |
| 5,804,045 A | 9/1998 | Orillon et al. |
| 5,879,915 A | 3/1999 | Loubiere et al. |
| 5,883,762 A | 3/1999 | Calhoun et al. |
| 5,928,806 A | 7/1999 | Olah et al. |
| 5,952,540 A | 9/1999 | Kyu et al. |
| 5,997,715 A | 12/1999 | Roberts et al. |
| 6,024,855 A | 2/2000 | Sharifan et al. |
| 6,099,990 A | 8/2000 | Denton et al. |
| 6,429,333 B1 | 8/2002 | Saari et al. |
| 6,660,680 B1 | 12/2003 | Hampden-Smith et al. |
| 6,706,657 B2 | 3/2004 | Commereuc et al. |
| 6,713,649 B1 | 3/2004 | Hladly et al. |
| 6,841,700 B2 | 1/2005 | Auer et al. |
| 6,867,329 B2 | 3/2005 | Auer et al. |
| 6,849,764 B2 | 6/2005 | Gurkaynak et al. |
| 6,906,222 B2 | 6/2005 | Slany et al. |
| 6,955,743 B2 | 10/2005 | Rousu et al. |
| 6,987,134 B1 | 1/2006 | Gagnon |
| 6,992,212 B2 | 1/2006 | Zehner et al. |
| 7,081,547 B2 | 7/2006 | Fujimoto et al. |
| 7,157,404 B1 | 1/2007 | Jun et al. |
| 7,241,365 B2 | 7/2007 | Auer et al. |
| 7,253,316 B2 | 8/2007 | Pastre et al. |
| 7,323,593 B2 | 1/2008 | Adami et al. |
| 7,351,860 B2 | 4/2008 | Adami et al. |
| 7,420,088 B2 | 9/2008 | Karl et al. |
| 7,459,590 B2 | 12/2008 | Olah et al. |
| 7,479,570 B2 | 1/2009 | Ogo et al. |
| 7,605,293 B2 | 10/2009 | Olah et al. |
| 7,608,743 B2 | 10/2009 | Olah et al. |
| 7,612,233 B2 | 11/2009 | Hauk et al. |
| 7,618,725 B2 | 11/2009 | Masel et al. |
| 7,704,269 B2 | 4/2010 | Olah et al. |
| 8,313,634 B2 | 11/2012 | Bocarsly et al. |
| 8,592,633 B2 | 11/2013 | Cole et al. |
| 8,956,990 B2 | 2/2015 | Masel et al. |
| 9,012,345 B2 * | 4/2015 | Masel .................. B01J 31/0292 502/5 |
| 9,267,212 B2 | 2/2016 | Twardowski et al. |
| 9,370,773 B2 | 6/2016 | Masel et al. |
| 9,464,359 B2 | 10/2016 | Masel et al. |
| 9,481,939 B2 * | 11/2016 | Masel .................. C25B 13/08 |
| 9,580,824 B2 | 2/2017 | Masel et al. |
| 9,834,623 B1 | 2/2017 | Masel et al. |
| 9,849,450 B2 | 12/2017 | Masel et al. |
| 9,943,841 B2 | 4/2018 | Masel et al. |
| 9,945,040 B2 | 4/2018 | Masel et al. |
| 9,982,353 B2 | 5/2018 | Masel et al. |
| 10,047,446 B2 | 8/2018 | Kaczur et al. |
| 10,147,974 B2 | 12/2018 | Masel et al. |
| 10,173,169 B2 * | 1/2019 | Masel .................. C25B 15/02 |
| 2003/0049509 A1 | 3/2003 | Divisek |
| 2004/0023104 A1 | 2/2004 | Kohler et al. |
| 2004/0031685 A1 | 2/2004 | Anderson et al. |
| 2004/0072683 A1 | 4/2004 | Kodas et al. |
| 2005/0277752 A1 | 12/2005 | Bringley |
| 2006/0096871 A1 | 5/2006 | Manoukian et al. |
| 2006/0234174 A1 | 10/2006 | Burrahm et al. |
| 2006/0235091 A1 | 10/2006 | Olah et al. |
| 2007/0036706 A1 | 2/2007 | Ogo et al. |
| 2007/0045125 A1 | 3/2007 | Hartvigsen et al. |
| 2007/0187247 A1 | 8/2007 | Lackner et al. |
| 2007/0259236 A1 | 11/2007 | Lang et al. |
| 2008/0039538 A1 | 2/2008 | Olah et al. |
| 2008/0103040 A1 | 5/2008 | Rodriguez et al. |
| 2008/0113244 A1 | 5/2008 | Yamashita et al. |
| 2008/0223727 A1 | 9/2008 | Oloman et al. |
| 2008/0287684 A1 | 11/2008 | Exner et al. |
| 2009/0014336 A1 | 1/2009 | Olah et al. |
| 2009/0016948 A1 | 1/2009 | Young |
| 2009/0169452 A1 | 7/2009 | Constantz et al. |
| 2009/0289211 A1 | 11/2009 | Fujioka et al. |
| 2010/0132556 A1 | 6/2010 | Constantz et al. |
| 2010/0133120 A1 | 6/2010 | Varney et al. |
| 2010/0135865 A1 | 6/2010 | Constantz et al. |
| 2010/0137457 A1 | 6/2010 | Kaplan |
| 2010/0187123 A1 | 7/2010 | Bocarsly et al. |
| 2010/0193370 A1 | 8/2010 | Olah et al. |
| 2010/0276287 A1 | 11/2010 | Manoukian et al. |
| 2011/0114501 A1 | 5/2011 | Teamey et al. |
| 2011/0114502 A1 | 5/2011 | Cole et al. |
| 2011/0114503 A1 | 5/2011 | Sivasanker et al. |
| 2011/0114504 A1 | 5/2011 | Sivasanker et al. |
| 2011/0226632 A1 | 9/2011 | Cole et al. |
| 2011/0237830 A1 | 9/2011 | Masel |
| 2012/0119410 A1 | 5/2012 | Yan et al. |

(56) References Cited

U.S. PATENT DOCUMENTS

| | | |
|---|---|---|
| 2012/0171583 A1 | 7/2012 | Bocarsly et al. |
| 2012/0186446 A1 | 7/2012 | Bara et al. |
| 2012/0308903 A1 | 12/2012 | Masel |
| 2013/0105304 A1 | 5/2013 | Kaczur et al. |
| 2013/0157174 A1 | 6/2013 | Masel et al. |
| 2013/0175181 A1 | 7/2013 | Kaczur |
| 2014/0206894 A1 | 7/2014 | Cole et al. |
| 2014/0206895 A1 | 7/2014 | Twardowski et al. |
| 2014/0206896 A1 | 7/2014 | Sivasankar et al. |
| 2014/0291163 A1 | 10/2014 | Kanan et al. |
| 2014/0370417 A1 | 12/2014 | Matsuda et al. |
| 2014/0378561 A1 | 12/2014 | Van Berchum et al. |
| 2015/0171453 A1 | 6/2015 | Chikashige et al. |
| 2015/0222002 A1* | 8/2015 | Graves .......... H01M 8/243 320/128 |
| 2015/0345034 A1 | 12/2015 | Sundara et al. |
| 2016/0107154 A1 | 4/2016 | Masel et al. |
| 2016/0108530 A1 | 4/2016 | Masel et al. |
| 2016/0251766 A1 | 9/2016 | Masel et al. |
| 2017/0037522 A1 | 2/2017 | Kaczur et al. |
| 2017/0117536 A1 | 4/2017 | Choi et al. |
| 2017/0128930 A1 | 5/2017 | Masel et al. |
| 2017/0183789 A1 | 6/2017 | Matthews et al. |
| 2017/0189898 A1 | 7/2017 | Masel et al. |
| 2017/0233881 A1 | 8/2017 | Masel et al. |
| 2017/0321334 A1 | 11/2017 | Kuhl et al. |
| 2018/0030187 A1 | 2/2018 | Wang et al. |
| 2018/0127668 A1 | 5/2018 | Masel |
| 2018/0316063 A1 | 11/2018 | Masel et al. |

FOREIGN PATENT DOCUMENTS

| | | |
|---|---|---|
| CA | 2821642 A1 | 6/2012 |
| CN | 1951986 A | 4/2007 |
| CN | 101250711 B | 11/2010 |
| CN | 102971451 A | 3/2013 |
| DE | 183856 C | 1/1906 |
| DE | 19754304 A1 | 6/1999 |
| EP | 0012215 B1 | 6/1980 |
| EP | 0151510 A1 | 8/1985 |
| EP | 0293230 A2 | 11/1988 |
| EP | 0323300 A1 | 7/1989 |
| GB | 2230782 A | 10/1990 |
| JP | S4848409 A | 5/1973 |
| JP | S4875513 A | 10/1973 |
| JP | S54138502 A | 10/1979 |
| JP | S54071098 A | 12/1979 |
| JP | S57119909 A | 7/1982 |
| JP | S58110684 A | 7/1983 |
| JP | S59219485 A | 12/1984 |
| JP | H0413883 A | 5/1990 |
| JP | H05093290 A | 4/1993 |
| JP | H09235568 A | 9/1997 |
| JP | H1017554 A | 1/1998 |
| JP | 2002306975 | 10/2002 |
| JP | H142002306975 A | 10/2002 |
| JP | H152003300913 A | 10/2003 |
| JP | H16127647 A | 4/2004 |
| JP | H162004127647 A | 4/2004 |
| JP | H192004533545 A | 11/2004 |
| JP | H18049157 A | 2/2006 |
| JP | H182006049157 A | 2/2006 |
| JP | H18351271 A | 12/2006 |
| JP | H182006351271 A | 12/2006 |
| JP | H19134164 A | 5/2007 |
| JP | H192007134164 A | 5/2007 |
| JP | H192007515283 A | 6/2007 |
| JP | H202008517749 A | 5/2008 |
| JP | H212009511740 A | 3/2009 |
| JP | H22517059 A | 5/2010 |
| JP | H222010517059 A | 5/2010 |
| JP | H242012017300 A | 1/2012 |
| JP | H242012138276 A | 7/2012 |
| JP | H252013525088 A | 6/2013 |
| WO | 2008110830 A1 | 9/2008 |
| WO | WO 2008110830 A1 | 9/2008 |
| WO | 2010007602 A1 | 1/2010 |
| WO | WO 2010007602 A1 | 1/2010 |
| WO | 2010063624 A1 | 6/2010 |
| WO | 2010063626 A1 | 6/2010 |
| WO | WO 2010063624 A1 | 6/2010 |
| WO | WO 2010063626 A1 | 6/2010 |
| WO | 2010014684 A2 | 12/2010 |
| WO | WO 2010014684 A2 | 12/2010 |
| WO | 2011120021 A1 | 9/2011 |
| WO | WO 2011120021 A1 | 9/2011 |
| WO | 2012006240 A1 | 1/2012 |
| WO | WO 2012006240 A1 | 1/2012 |
| WO | 2013006711 A1 | 1/2013 |
| WO | WO 2013006711 A1 | 1/2013 |
| WO | 2012118065 A1 | 7/2014 |
| WO | WO 2012118065 A1 | 7/2014 |
| WO | 2016039999 A1 | 3/2016 |
| WO | 2019051609 A1 | 3/2019 |

OTHER PUBLICATIONS

U.S. Appl. No. 16/024327, Office Action dated May 4, 2020 ("20200504USOA").

EP App. No. 157226077, Office Action dated May 7, 2020 ("20200507EPOA").

EP App. No. 16782111.5, Office Action dated Mar. 20, 2020 ("20200320EPOA").

JP App. No. 2018-145931, Office Action dated May 19, 2020 ("20200519JPOA").

Wilson et al., "Thin-Film Catalyst Layers for Polymer Electrolyte Fuel Cell Electrodes", J. of Applied Electrochem. 22 (1992), pp. 1-7.

Komatsu et al., "Preparation of Cu-Solid Polymer Electrolyte Composite Electrodes and Application to Gas-Phase Electrochemical Reduction of $CO_2$," Electrochimica Acta, vol. 40, No. 6, (1995), pp. 745-753.

Sata et al., "Preparation and Properties of Anion Exchange Membranes Having Pyridinium or Pyridinium Derivatives as Anion Exchange Groups", J. of Polymer Sci. Part A: Polymer Chem., vol. 36, No. 1, (1998), pp. 49-58.

Lee et al., "Humidity-Sensitive Properties of New Polyelectrolytes Based on the Copolymers Containing Phosphonium Salt and Phosphine Function", J. Applied Polymer Sci. 89 (2003), pp. 1062-1070.

Torres et al., "Carbonate Species as OH-Carriers for Decreasing the pH Gradient between Cathode and Anode in Biological Fuel Cells", Environmental Sci.& Tech., vol. 42, No. 23, (2008), pp. 8773-8777.

Li et al., "Novel Anion Exchange Membranes Based on Polymerizable Imidazolium Salt for Alkaline Fuel Cell Applications", J. Mater. Chem. 21 (2011), pp. 11340-11346.

Lin et al., "Alkaline Stable C2-Substituted Imidazolium-Based Anion-Exchange Membranes", Chem. Mater. 25 (2013) pp. 1858-1867.

Koshikawa et al., "Counter-anion Effect on the Properties of Anion-Conducting Polymer Electrolyte Membranes Prepared by Radiation-Induced Graft Polymerization", Macromol. Chem. Phys. 214, (2013) pp. 1756-1762.

Parrondo et al, "Hydrogen Production by Alkaline Membrane Water Electrolysis", 224th ECS Meeting, (2013).

Varcoe et al., "Anion-Exchange Membranes in Electrochemical Energy Systems," Energy and Env. Sci., (2014) pp. 3135-3191.

Office Action dated Mar. 20, 2020 issued in connection with European application No. 16782111.5.

Office Action dated May 7, 2020 issued in connection with European application No. 15722607.7.

Office Action dated May 19, 2020 issued in connection with Japanese application No. 2018-145931.

Mahmood et al, "Use of gas-diffusion electrodes for high-rate electrochemical reduction of carbon dioxide. II Reduction at metal phthalocyanine-impregnated electrodes", J. of Applied Electrochem., vol. 17, No. 6, (1987), pp. 1223-1227.

(56) References Cited

OTHER PUBLICATIONS

Chen et al. "A Concept of Supported Amino Acid Ionic Liquids and their Application in Metal Scavenging and Heterogeneous Catalysis", J. Am. Chem. Soc., 129, (2007), pp. 13879-13886.
Narayanan et al., "Electrochemical Conversion of Carbon Dioxide to Formate in Alkaline Polymer Electrolyte Membrane Cells", J. of the Electrochemical Society, vol. 158, No. 2, (2011), p. A167.
Yan et al., "Imidazolium-Functionalized Poly(Ether Ether Ketone) as Membrane and Electrode Ionomer for Low-Temperature Alkaline Membrane Direct Methanol Fuel Cell", J. of Power Sources, vol. 250. (2013), pp. 90-97.
International Search Report and Written Opinion dated Feb. 15, 2013 issued in connected with International Application No. PCT/US2012/043651.
International Preliminary Report on Patentability dated Dec. 23, 2013 issued in connected with International Application No. PCT/US2012/043651.
Ganesh, "Conversion of Carbon Dioxide Into Methanol—A Potential Liquid Fuel: Fundamental Challenges and Opportunities (a Review)", Renewable and Sustainable Energy Reviews, vol. 31, (2014), pp. 221-257.
Office Action dated Jul. 28, 2015 in connection with Japanese Application 2013-501536.
Li et al., "Electrolysis of CO2 to Syngas in Bipolar Membrane-Based Electrochemical Cells", ACS Energy Lett., vol. 1 (2016) pp. 1149-1153.
Vermaas et al., "Synergistic Electrochemical CO2 Reduction and Water Oxidation with a Bipolar Membrane", ACS Energy Lett., vol. 1 (2016) pp. 1143-1148.
Zhou et al., "Solar-Driven Reduction of 1 atm of CO2 to Formate at 10% Energy-Conversion Efficiency by Use of a TiO2-Protected III-V Tandem Photoanode in Conjunction with a Bipolar Membrane and a Pd/C Cathode", ACS Energy Lett., vol. 1 (2016) pp. 764-770.
Office Action dated Feb. 1, 2016 in connection with Chinese Application No. 201180023851.2.
Patent Examination Report No. 4 dated Feb. 2, 2016 in connection with Australian Application No. 2012272770.
Office Action dated Sep. 13, 2016 issued in connection with Korean application No. 10-2016-7022952.
Decision to Grant dated Nov. 10, 2016 in connection with Japanese App. No. 2013-518759.
Partial International Search Report and Written Opinion dated Nov. 24, 2016 issued in connection with International Application No. PCT/US16/45210.
International Search Report and Written Opinion dated Jan. 20, 2017 issued in connection with International Application No. PCT/US16/45210.
International Preliminary Report on Patentability dated May 4, 2017 issued in connected with International Application No. PCT/US2015/014328.
International Preliminary Report on Patentability dated May 4, 2017 issued in connection with International Application No. PCT/US2015/026507.
Office Action dated May 29, 2017 issued in connection with Korean application No. 10-2016-7022952.
Partial International Search Report and Written Opinion dated Jun. 22, 2017 in connection with International Application No. PCT/US17/25624.
Patent Examination Report No. 1 dated Jun. 29, 2017 issued in connection with Australian application No. 2015337093.
International Search Report and Written Opinion dated Jul. 12, 2017 issued in connection with International Application No. PCT/US17/25628.
International Search Report and Written Opinion dated Aug. 16, 2017 in connection with International Application No. PCT/US17/25624.
Office Action dated Sep. 13, 2017 issued in connection with Canadian application No. 2941423.
Decision to Grant dated Oct. 31, 2017 issued in connection with Japanese application No. 2015-232576.
Li et al., "Bipolar Membranes Inhibit Product Crossover in CO2 Electrolysis Cells", Adv. Sustainable Syst., (2018) pp. 1-5.
Salvatore et al., "Electrolysis of Gaseous CO2 to CO in a Flow Cell with a Bipolar Membrane", ACS Energy Lett., vol. 3 (2018) pp. 149-154.
Office Action dated Jan. 25, 2018 in connection with Canadian Application No. 2,802,893.
Office Action dated Feb. 6, 2018 issued in connection with Japanese application No. 2016-559881.
Office Action dated Mar. 13, 2018 issued in connection with European application No. 15722607.7.
Office Action dated Mar. 21, 2018 issued in connection with Chinese application No. 201580015121.6.
Office Action dated May 23, 2018 issued in connection with Canadian application No. 2941423.
Patent Examination Report No. 2 dated Jun. 26, 2018 issued in connection with Australian application No. 2015337093.
International Preliminary Report on Patentability dated Oct. 18, 2018 issued in connection with International Application No. PCT/US16/45210.
International Preliminary Report on Patentability dated Oct. 18, 2018 issued in connection with International Application No. PCT/US17/25624.
International Preliminary Report on Patentability dated Oct. 18, 2018 in connection with International Application No. PCT/US17/25628.
International Preliminary Report on Patentability dated Oct. 18, 2018 issued in connection with International Application No. PCT/US17/25630.
Decision to Grant dated Nov. 6, 2018 in connection with Japanese App. No. 2016-238639.
Office Action dated Nov. 13, 2018 issued in connection with European application No. 15722607.7.
Decision to Grant dated Dec. 4, 2018 issued in connection with Japanese application No. 2016-559881.
Office Action dated Dec. 24, 2018 issued in connection with Chinese application No. 201580015121.6.
Patru et al., "Design Principles of Bipolar Electrochemical Co-Electrolysis Cells for Efficient Reduction of Carbon Dioxide from Gas Phase at Low Temperature", J. of the Electrochemical Society, vol. 166, (2019) pp. F34-F43.
Patent Examination Report No. 1 dated Jan. 21, 2019 issued in connection with Australian application No. 2016401931.
Patent Examination Report No. 1 dated Jan. 25, 2019 issued in connection with Australian application No. 2017246207.
Office Action dated Feb. 8, 2019 issued in connection with Canadian application No. 2941423.
European Office Action dated Mar. 27, 2019 in connection with European App. No. 11713569.9.
Seshadri et al., "A New Homogeneous Electrocatalyst for the Reduction of Carbon Dioxide to Methanol at Low Overpotential", J. Electroanalytical Chem. 372 (1994), pp. 145-150.
Xu et al., "Effects of Imidazolium Salts as Cocatalysts on the Copolymerization of CO2 with Epoxides Catalyzed by Salen) CrIIICI Complex", Polymer 48 (2007), pp. 3921-3924.
Yoshizawa-Fujita et al., "A New Class of Proton-Conducting Ionic Plastic Crystals Based on Organic Cations and Dihydrogen Phosphate", Electrochem. Communications 9 (2007), pp. 1202-1205.
Chu et al., "Fixation of CO2 by Electrocatalytic Reduction and Electropolymerization in Ionic Liquid-H20 Solution", ChemSusChem 1 (2008), pp. 205-209.
Delacourt et al., "Design of an Electrochemical Cell Making Syngas (CO+H-2) from CO2 and H20 Reduction at Room Temperature", J. Electrochem. Soc. 155 (2008), pp. B42-B49.
Delacourt et al., "Mathematical Modeling of a Cation-Exchange Membrane Containing Two Cations", J. Electrochem. Soc. 155 (2008), pp. B1210-B1217.
Fukuzumi, "Bioinspired Energy Conversion Systems for Hydrogen Production and Storage", Eur. J. Inorg. Chem. J008 (2008), pp. 1351-1362.
Hori, "Electrochemical CO2 Reduction on Metal Electrodes", Modem Aspects of Electrochem. 42 (2008), pp. 89-189.

(56) References Cited

OTHER PUBLICATIONS

Ikeda et al., "Electrochemical Reduction of Carbon Dioxide Using Gas Diffusion Electrodes Loaded with Fine Catalysts", Nanoscience and Nanotechnology 1136 (2008), pp. 108-113.
Jiang et al., "Solvent-Free Synthesis of Substituted Ureas from CO2 and Amines with a Functional Ionic Liquid as the Catalyst", Green Chem. 10 (2008), pp. 465-469.
Kinge et al., "Dependence of CO Oxidation on PI Nanoparticle Shape: A Shape-Selective Approach to the Synthesis of PEMFC Catalysts", Applied Organometallic Chem. 22 (2008), pp. 49-54.
Oloman et al., "Electrochemical Processing of Carbon Dioxide", ChemSusChem 1 (2008), pp. 385-391.
O'Mahony et al., "The Electrochemical Reduction of Hydrogen Sulfide on Platinum in Several Room Temperature Ionic Liquids", The J. Phys. Chem. C 112 (2008), pp. 7725-7730.
Rezaei et al., "Effects of Tetrabutylammonium Hydrogen Sulfate as an Electrolyte Additive on the Electrochemical Behavior of Lead Acid Battery", J. Solid State Electrochem. 12 (2008), pp. 1663-1671.
Scheijen et al., "The Electrooxidation of Small Organic Molecules on Platinum Nanoparticles Supported on Gold: Influence of Platinum Deposition Procedure", J. Solid State Electrochem. 12 (2008), pp. 483-495.
Silvester et al., "Electrochemical Reduction of Benzoic Acid and Substituted Benzoic Acids in Some Room Temperature Ionic Liquids", The J. Phys. Chem. C 112 (2008), pp. 12966-12973.
Solla-Gullon et al., "Shape-Dependent Electrocatalysis: Methanol and Formic Acid Electrooxidation on Preferentially Oriented PI Nanoparticles", Phys. Chem. Chem. Phys. 10 (2008), pp. 3689-3698.
Sun et al., "Hydroxyl-Functionalized Ionic Liquid: A Novel Efficient Catalyst for Chemical Fixation of CO2 to Cyclic Carbonate", Tetrahedron Lett. 49 (2008), pp. 3588-3591.
Tian et al., "Platinum Metal Catalysts of High-Index Surfaces: From Single-Crystal Planes to Electrochemically Shape controlled Nanoparticles", J. Phys. Chem. C 112 (2008), pp. 19801-19817.
Wong et al., "A Robust Ionic Liquid as Reaction Medium and Efficient Organocatalyst for Carbon Dioxide Fixation", ChemSusChem 1 (2008), pp. 67-70.
Yang et al., "Electrodeposition of Tin and Antimony in 1-Ethyl-3-Methylimidazolium Tetrafluoroborate Ionic Liquid", J. Appl. Electrochem 38 (2008), 537-542.
Zhang et al., "Electrochemical Activation of CO2 in Ionic Liquid (BMIMBF4): Synthesis of Organic Carbonates Under Mild Conditions", Green Chem. 10 (2008), pp. 202-206.
Zhang et al., "Hydrogenation of Carbon Dioxide is Promoted by a Task-Specific Ionic Liquid", Angewandle. Chem. Int. Ed. 47 (2008), pp. 1127-1129.
Barrosse-Antle et al., "Reduction of Carbon Dioxide in 1-Butyl-3-Methylimidazolium Acetate", Chem. Commun. (2009), pp. 3744-3746.
Cheung et al., "Electrocatalytic Reduction of Carbon Dioxide by a Polymeric Film of Rhenium Tricarbonyl Dipyndylamine", J. Organometallic Chem. 694 (2009), pp. 2842-2845.
Haerens et al., "Electrochemical Decomposition of Choline Chloride Based Ionic Liquid Analogues", Green Chem. 11 (2009), pp. 1357-1365.
Innocent et al., "Electro-Reduction of Carbon Dioxide to Formate on Lead Electrode in Aqueous Medium", J of Applied Electrochem. 39 (2009), pp. 227-232.
Kaneco et al., "Photoelectrochemical Reduction of CO2 at P-Lnp Electrode in Copper Particle-Suspended Methanol" Chem. Eng. J. 148 (2009), pp. 57-62.
Liu et al., "Observation of Surface Structural Changes of PI Octahedron Nanoparticles and its Effect in Electrocatalyst Oxidation of Methanol", Catalysis Communications 10 (2009), pp. 1244-1247.
Lukaszewski et al., "Electrosorption of Carbon Dioxide on Platinum Group Metals and Alloys—A Review", J. Solid State Electrochem. 13 (2009), pp. 813-827.

Ma et al., "A Short Review of Catalysis for CO2 Conversion", Catal. Today 148 (2009), pp. 221-231.
Ohya et al., "Electrochemical Reduction of CO2 in Methanol with Aid of CuO and Cu20", Catalysis Today 148 (2009), pp. 329-334.
Photinon et al., "Thick-Film carbon dioxide sensor via anodic adsorbate stripping technique and its structural dependence", Sensors 9 (2009), pp. 7203-7216.
Rakowski et al., Development of Molecular Electrocatalysts for CO2 Reduction and H2 Production/Oxidation Acc. Chem. Res. 42 (2009), pp. 1974-1982.
Rezaei et al., Application of Ionic Liquids as an Electrolyte Additive on the Electrochemical Behavior of Lead Acid Battery. J. Power Sources, 187(2) (2009), pp. 605-612.
Yan, Adsorption of CO2 on the rutile (110) surface in ionic liquid. A molecular dynamics simulation J. Phys. Chem. C 113 (2009), pp. 19389-19392.
Yuan, Electrochemical activation of carbon dioxide for synthesis of dimethyl carbonate in an ionic liquid Electrochimica Acta 54 (2009), pp. 2912-2915.
Zhang et al., Chiral ionic liquids improved the asymmetric cycloaddition of CO2 to epoxides Green Chem. 11 (2009), pp. 935-938.
Zhang, Hydrogenation of CO2 to formic acid promoted by a diamine-functionalized ionic liquid ChemSusChem 2 2009), pp. 234-238.
Cahill et al., "Investigation of proton dynamics and the proton transport pathway in choline dihydrogen phosphate using solid-slate NMR", Physical Chem. Chemical Physics 12 (2010), pp. 5431-5438.
Cole et al., Using a one electron shuttle for the multielectron reduction of CO2 to methanol: kinetic, mechanism and structural insights, J. Am. Chem. Soc. 132, (2010), pp. 11539-11551.
Li, "Electrocatalytic Reduction of CO2 to Small Organic Molecule Fuels on Metal Catalysts", Advances in CO2 Conversion and Utilization (2010), pp. 55-76.
Lopez-Cudero et al., "CO electrooxidation on carbon supported platinum nanoparticles: Effect of aggregation", J. Electroanalytical Chem. 644 (2010), pp. 117-126.
Ogura et al., "CO2 Attraction by Specifically Adsorbed Anions and Subsequent Accelerated Electrochemical Reduction", Electrochimica Acta 56 (2010), pp. 381-386.
Tian et al., "Direct Electrodeposition of Tetrahexahedral Pd Nanocrystals with High-Index Facets and High Catalytic Activity for Ethanol Electrooxidation", J. Am. Chem. Soc. 132 (2010), pp. 7580-7581.
Gazsi et al., "Decomposition and Reforming of Formic Acid on Supported Au Catalysts: Production of CO-Free H2", J. Phys. Chem. C 115 (2011), pp. 15459-15466.
Koper. "Structure Sensitivity and Nanoscale Effects in Electrocatalysis". Nanoscale 3 (2011), pp. 2054-2073.
Morris et al., "Electrocatalytic Carbon Dioxide Activation: The Rate-Determining Step of Pyridinium-Catalyzed CO2 Reduction", ChemSusChem 4 (2011), pp. 191-196.
Perez et al., "Particle Size Effect for Ethanol Electro-Oxidation on Pt/C Catalysts in Half-Cell and in a Single Direct Ethanol Fuel Cell", J. Electroanalytical Chem. 654 (2011), pp. 108-115.
Rosen et al., "Ionic Liquid-Mediated Selective Conversion of CO2 to CO at Low Overpotentials", Science 334 (2011), pp. 643-644.
Sabatier et al., "Chimie Organique.—Sur la Decomposition Catalytique de l'acide Formique", Comptes Rendus Hebdomadaires Des Seances De L'Academie Dessciences 152 (1911), pp. 1212-1215.
Pease et al., "The Catalytic Combination of Ethylene and Hydrogen in the Presence of Metallic Copper 111. Carbon Monoxide as a Catalyst Poison", J. Am. Chem. Soc. 47 (1925), pp. 1235-1240.
Urey et al., "Some Reactions of Atomic Hydrogen", J. of the Am. Chem. Soc. 51 (1929), pp. 3286-3290.
Udupa et al., "The Electrolytic Reduction of Carbon Dioxide to Formic Acid", Electrochimica Acta 16 (1971), pp. 1593-1598.
Bregoli, "The Influence of Platinum Crystallite Size on the Electrochemical Reduction of Oxygen in Phosphoric Acid", Electrochimica Acta 23 (1978), pp. 489-492.
Bard et al., Electrochemical Methods Fundamentals and Applications (1980), pp. 22-24.

(56) References Cited

OTHER PUBLICATIONS

Fisher et al., "Electrocatalytic Reduction of Carbon Dioxide by Using Macrocycles of Nickel and Cobalt", J. Am. Chem. Soc., vol. 102, No. 24 (1980), pp. 7361-7363.
Weiss et al., "Formose Sugars from Formaldehyde", Applied Catalysis 1 (1981), pp. 237-246.
Eggins et al., "Voltammetry of Carbon Dioxide: A General Survey of Voltammetry at Different Electrode Materials in Different Solvents", J. Electroanalytical Chem. 148 (1983), pp. 17-24.
Danly, "Development and Commercialization of the Monsanto electrochemical Adiponitrile Process", J. Electrochem. Soc. 131 (1984), pp. 435C-442C.
Franklin et al., "The Effect of Quaternary Ammonium Salts on the Anodic Oxidation of Ethanol", Surface Tech. 24(2) (1985), pp. 143-155.
Chandrasekaran, "In-situ Spectroscopic Investigation of Adsorbed Intermediate Radicals in Electrochemical Reactions: Carbon Dioxide (1–) (CO2–) on Platinum", Surface Science 185 (1987), pp. 495-514.
Ikeda et al., "Selective Formation of Formic Acid. Oxalic Add, and Carbon Monoxide by Electrochemical Reduction of Carbon Dioxide", Bull. Chem. Soc. Japan, vol. 60 (1987), pp. 2517-2522.
Dewulf et al., "The electrochemical reduction of CO2 to CH4 and C2H4 at Cu/Nafion Electrodes (Solid Polymer Electrolyte structures)", Catalysis Letters 1 (1988), pp. 73-80.
Dewulf et al., "Electrochemical and Surface Studies of Carbon Dioxide Reduction to Methane and Ethylene at Copper Electrodes in Aqueous Solutions", J. Electrochem. Soc. 136 (1989), pp. 1686-1691.
Azuma et al., "Electrochemical Reduction of Carbon Dioxide on Various Metal, Electrodes in Low-Temperature Aqueous KHC03 Media", J. Electrochem. Soc. 137 (1990), pp. 1772-1778.
Hori et al., "Electrochemical Evidence of Intermediate Formation of Adsorbed Carbon Monoxide in Cathodic Reduction of CO2 at a Nickel Electrode", Electrochimica Acta 35 (1990), pp. 1777-1780.
Kinoshita, "Particle Size Effects for Oxygen Reduction on Highly Dispersed Platinum in Acid Electrolytes", J. Electrochem. Soc. 137 (1990), pp. 845-848.
Noda et al., "Electrochemical Reduction of Carbon Dioxide at Various Metal Electrodes in Aqueous Potassium Hydrogen Carbonate Solution", Bull. Chem. Soc. Jpn. 63 (1990), pp. 2459-2462.
Dubois et al., "Electrochemical Reduction of Carbon Dioxide Catalyzed by [Pd(Triphosphine)(Solvent)](BF4)2 Complexes: Synthetic and Mechanistic Studies", J. Am. Chem. Soc. 113 (1991), pp. 8753-8764.
Derien et al., "Activation of Carbon Dioxide: Nickel-Catalyzed Electrochemical Carboxylation of Diynes", J. Organic Chem. 58 (1993), pp. 2578-2588.
Kabbabi et al., "Particle-Size Effect for Oxygen Reduction and Methanol Oxidation on PI/C Inside a Proton Exchange Membrane", J. Electroanalytical Chem. 373 (1994), pp. 251-254.
Meiwes-Broer, "Work Functions of Metal Clusters", Hyperfine Interactions 89 (1994), pp. 263-269.
Podlovchenko et al., "Electroreduction of Carbon Dioxide on Palladium Electrodes at Potentials Higher than the Reversible Hydrogen Potential". J. Electroanalytical Chem. 373 (1994), pp. 185-187.
Saeki et al., "Electrochemical Reduction of Liquid CO2. Drastic Enhancement of Current Density", J. Electrochem. Soc. 141 (1994), pp. L 130-L132.
Dietz et al., "Influence of Substituted Benzaldehydes and their Derivatives as Inhibitors for Hydrogen Evolution in Lead/Acid Batteries", J. Power Sources 53 (1995), pp. 359-365.
Idriss et al., "Two Routes to Formaldehyde from Formic Acid on Ti0 (001) Surfaces", Surface Science 348 (1996), pp. 39-48.
Eggins et al., "Improved Yields of Oxalate, Glyoxylale and Glycolale from the Electrochemical Reduction of Carbon Dioxide in Methanol", J. Applied Electrochem. 27 (1997), pp. 706-712.
Furuya et al., "High Performance Ru—Pd Catalysts for CO2 Reduction at Gas-Diffusion Electrodes", J. Electroanalytical Chem. 431 (1997), pp. 39-41.
Hoshi et al., "Electrochemical Reduction of CO2 on Single Crystal Electrodes of Silver Ag(111), Ag(100) and Ag(110)", J. Electroanalytical Chem. 440 (1997), pp. 283-286.
Popic et al., "Reduction of Carbon Dioxide on Ruthenium Oxide and Modified Ruthenium Oxide Electrodes in 0.5 M NaHC03", J. Electroanalytical Chem. 421 (1997), pp. 105-110.
Sung et al., "Structure of Chemisorbed Sulfur on a PI(III) Electrode", J. Am. Chem. Soc. 119 (1997), pp. 194-200.
Kaneco et al., "Electrochemical Conversion of Carbon Dioxide to Formic Acid on Pb in KOH/Methane Electrolyte Al Ambient Temperature and Pressure", Energy 23 (1998), pp. 1107-1112.
Karp et al., "Isolation of Nucleic Acids Using Silica-Gel Based Membranes: Methods Based on the Use of QIAamp Spin Columns", Molecular Tools for Screening Biodiversity (1998), pp. 59-63.
Smolinski et al., "Effect of Surface Order on Adsorption of Sulfate Ions on Silver Electrodes", J. Electroanalytical Chem. 442 (1998), pp. 41-47.
Sobkowski et al., "Interaction of Sulfate Ions with Monocrystalline Silver Electrodes", Colloids Surfaces A: Physicochem. and Eng. Aspects 134 (1998), pp. 39-45.
Yano et al., "Effect of Additives in Zinc Alloy Powder on Suppressing Hydrogen Evolution", J. Power Sources 7 4 (1998), pp. 129-134.
Ikeda et al., "Zinc Ion Effect on Electrochemical Reduction of Carbon Dioxide at Zinc Electrode in Aqueous Solutions", Electrochemistry (Tokyo) 67 (1999), pp. 27-33.
Kaneco et al., "Electrochemical Reduction of Carbon Dioxide to Ethylene with High Faradaic Efficiency at a Cu Electrode in CsOH/Melhanol", Electrochimica Acta 44 (1999), 4701-4706.
Welton, "Room-Temperature Ionic Liquids. Solvents for Synthesis and Catalysis", Chem. Rev. 99 (1999), pp. 2071-2083.
Hoshi et al., "Electrochemical Reduction of Carbon Dioxide at a Series of Platinum Single Crystal Electrodes", Electrochimica Acta 45 (2000), pp. 4263-4270.
Kiss, "Palladium-Catalyzed Reppe Carbonylalion", Chem. Rev. 101 (2001), pp. 3435-3456.
Masel, "Chemical Kinetics and Catalysis", Wiley (2001), pp. 702-742.
Ishida et al., "High-Temperature Electrochemical Reduction of Carbon Dioxide Using an Ionic Liquid". The Chem. Soc. of Jpn, Proceeding of 82th Autumn Meeting, Sep. 10, 2002, pp. 46, 1A6-01.
Takahashi et al., "Electrochemical Reduction of CO2 at Copper Single Crystal Cu(S)-[n(111)×(111 )] and Cu(S)-[n(110)×(100)] Electrodes", J. of Electroanalytical Chem. 533 (2002), pp. 135-143.
Yang et al., "Electrochemical Activation of Carbon Dioxide in Ionic Liquid: Synthesis of Cyclic Carbonates at Mild Reaction Conditions", Chem. Communications. (2002), pp. 274-275.
Chaplin et al., "Effects of Process Conditions and Electrode Material on Reaction Pathways for Carbon Dioxide Electroreduction with Particular Reference to Formate Formation", J. Applied Electrochem. 33 (2003), pp. 1107 1123.
Cherstiouk et al., "Model Approach to Evaluate Particle Size Effects in Electrocalalysis: Preparation and Properties of PI Nanoparticles Supported on GC and HOPG", Electrochimica Acta 48 (2003), pp. 3851-3860.
Davis et al., "Commercially Available Salts as Building Blocks for New Ionic Liquids", ACS Symp Ser. 856 (2003), pp. 100-107.
Lee et al., "Synthesis and Activities of Rutile IrO2 and RuO2 Nanoparticles for Oxygen Evolution in Acid and Alkaline Solutions", The Journal of Physical Chem. Letters, (2012) pp. 399-404.
Office Action dated Jun. 22, 2020 issued in connection with Chinese application No. 201580015121.6.
Office Action dated Jul. 3, 2020 issued in connection with Korean application No. 10-2017-7035452.
Office Action dated Jul. 27, 2020 issued in connection with Korean application No. 10-2018-7031597.
Office Action dated Oct. 1, 2020 issued in connection with European application No. 16782111.5.
Office Action dated Sep. 2, 2020 issued in connection with Korean application No. 10-2018-7031595.
Solla-Gullon et al., "Shape Dependent Electrocatalysis", Annual Reports on the Progress of Chem.—Section C 107 (2011), pp. 263-297.

(56) References Cited

OTHER PUBLICATIONS

Zhang et al., "Imidazolium functionalized polysulfone anion exchange membrane for fuel cell application", J. Mater. Chem. 21 (2011) pp. 12744-12752.
International Search Report and Written Opinion of the International Searching Authority dated Jul. 6, 2011 and dated Sep. 26, 2012 in connection with PCT/US2011/030098.
International Search Report and Written Opinion of the International Searching Authority dated Oct. 31, 2011 in connection with PCT/US2011/042809.
Chen et al., "Role of Surface Defect Sites: From Pt Model Surfaces to Shape-Controlled Nanoparticles", Chem. Sci. 2012), pp. 136-147.
Singh et al., "Comparison of Oxygen Reduction Reaction at Silver Nanoparticles and Polycrystalline Silver Electrodes in Alkaline Solution", J. Phys. Chem. C 116 (2012), pp. 10656-10663.
Yu et al., "Carboxylation of Terminal Alkynes with Carbon Dioxide Catalyzed by Poly(N-Heterocyclic Carbene)-Supported Silver Nanoparticles", Adv. Synth. Catal. 354 (2012), pp. 969-974.
Deng et al., "Linked Strategy for the Production of Fuels via Formose Reaction", Sci. Reports 3 (2013), p. 1244.
Zhu et al., "Monolayers of choline chloride can enhance desired electrochemical reactions and inhibit undesirable ones", Electrochimica Acta 96 (2013) pp. 18-22.
International Preliminary Report on Patentability dated Jan. 3, 2013 in connection with International Application No. PCT/US2011/042809.
International Preliminary Report on Patentability dated Jan. 3, 2013 in connection with International Application No. PCT/US2011/030098.
Third-Party Submissions Under 37 CFR 1.290, submitted on Sep. 17 and 18, 2013, in connection with co-owned 6 U.S. U.S. Appl. No. 12/830,338, and Concise Description of Relevance for each of the references cited in the Third Party Submissions.
International Search Report and Written Opinion dated May 16, 2014 in connection with International Application No. PCT/US2013/061506.
International Search Report and Written Opinion dated Jun. 17, 2014 in connection with International Application No. PCT/US2014/018067.
Office Action dated Aug. 5, 2014 in connection with Chinese Application No. 201180023851.2.
Patent Examination Report dated Nov. 5, 2014 in connection with Australian Application No. 2011276362.
Patent Examination Report No. 1 dated Dec. 12, 2014 in connection with Australian Application 2011230545.
Office Action dated Dec. 22, 2014, in connection with Chinese Application No. 201180033161.5.
Office Action dated Jan. 27, 2015 in connection with Japanese Application 2013-501536.
Patent Examination Report No. 1 dated Feb. 3, 2015 in connection with Australian Application No. 2012272770.
Office Action dated Jun. 2, 2015 in connection with Japanese Application No. 2013-518759.
Office Action dated Oct. 16, 2015 in connection with Chinese Application No. 201180023851.2.
Office Action dated Feb. 16, 2016 in connection with Japanese Application No. 2013-518759.
Office Action dated Oct. 16, 2015 in connection with Chinese Application No. 2011800331615.
Patent Examination Report No. 2 dated Jan. 8, 2016 in connection with Australian Application No. 2012272770.
Patent Examination Report No. 3 dated Jan. 28, 2016 in connection with Australian Application No. 2012272770.
Notice of Acceptance dated Mar. 2, 2016 in connection with Australian Application No. 2011276362.
Office Action dated Apr. 25, 2016 in connection with Canadian Application No. 2,794,105.
Notification of Grant dated Jun. 14, 2016 in connection with Chinese patent application No. 201180033161.5.
Office Action dated Aug. 1, 2016 in connection with Korean Application No. 10-2012-7027866.
Patent Examination Report No. 1 dated Aug. 2, 2016 in connection with Australian Application No. 2016200673.
Office Action dated Dec. 20, 2016, in connection with Japanese Application No. 2015-232576.
Office Action dated Mar. 31, 2017, in connection with European Patent Application No. 11713569.9.
Office Action dated Apr. 5, 2017 in connection with European Application No. 11743389.6-1360.
Office Action dated May 25, 2017 in connection with Canadian Application No. 2,802,893.
Office Action dated May 29, 2017 in connection with Korean Application No. 10-20137002749.
Office Action dated Jun. 8, 2017, in connection with Canadian Patent Application No. 2,794,105.
International Search Report and Written Opinion dated Jun. 22, 2017 in connection with International Application No. PCT/US2017/025630.
Examination Report No. 2 dated Jul. 21, 2017 in connection with Australian Application No. 2016200673.
International Search Report and Written Opinion dated Jul. 6, 2015 in connection with International Application PCT/US2015/014328.
International Search Report and Written Opinion dated Jul. 20, 2015 in connection with International Application PCT/US2015/026507.
Office Action dated Jan. 30, 2018 in connection with Japanese Application No. 2016-238639.
Examination Report dated Feb. 27, 2018 in connection with Indian Application No. 733/CHENP/2013.
Lee et al., "Humidity-sensitive properties of new polyelectrolytes based on the copolymers containing phosphonium salt and phosphine function", J. Applied Polymer Science 89 (2003), pp. 1062-1070.
Wang et al., "Water-Retention Effect of Composite Membranes with Different Types of Nanometer Silicon Dioxide" Electrochemical and Solid-State Letters 11 (2008), p. B201.
Chen et al., "Composite Blend Polymer Membranes withIncreased Proton Selectivity and Lifetime for Vanadium Redox Flow Batteries", J. of Power Sources 231 (2013) pp. 301-306.
Sarode et al., "Designing Alkaline Exchange Membranes from Scratch", The Electrochemical Society, 220th ECS Meeting (2011).
Luo et al., "Quaternized poly(methyl methacrylate-co-butyl acrylate-co-vinylbenzyl chloride) membrane for alkaline fuel cells", J. Power Sources. 195 (2010), pp. 3765-3771.
U.S. Appl. No. 16/552,952, Office Action dated Sep. 2, 2020 ("20200902USOA").
CN App. No. 201580015121.6, Office Action dated Jun. 22, 2020 ("20200622CNOA").
EP App. No. 16782111.5, Office Action dated Oct. 1, 2020 ("20201001EPO").
KR App. No. 10-2017-7035452, Office Action dated Jul. 3, 2020 ("20200703KROA").
KR App. No. 10-2018-7031595, Office Action dated Sep. 2, 2020 ("20200902KROAb").
KR App. No. 10-2018-7031597, Office Action dated Jul. 27, 2020 ("20200727KROA").
Hori et al., "Electrochemical Reduction of Carbon Dioxide at Various Series of Copper Single Crystal Electrodes", J. Molecular Catalysis A: Chem. 199 (2003), pp. 39-47.
Hoshi et al., "Electrochemical Reduction of Carbon Dioxide on Kinked Stepped Surfaces of Platinum Inside the Stereographic Triangle", J. Electroanalytical Chem. 540 (2003), pp. 105-110.
Kaneco et al. "Carbon Dioxide Sequestration Technology by Electrochemical Conversion at Cadmium Electrode in Methanol Under Mild Conditions", Photo/Electrochem. & Photo Biology in Environment, Energy and Fuel (2003), pp. 181-189.
Liu et al., "General Rules for Predicting Where a Catalytic Reaction Should Occur on Metal Surfaces: A Density Functional Theory Study of C—H and C—0 Bond Breaking/Making on Flat, Stepped and Kinked Metal Surfaces", J. Am. Chem. Soc. 125 (2003), pp. 1958-1967.
Magdesieva et al., "Lutetium Monophthalocyanine and Diphthalocyanine Complexes and Lithium Naphthalocyanine as

(56) References Cited

OTHER PUBLICATIONS

Catalysts for Electrochemical CO2 Reduction", J. of the Electrochem. Soc. 150 (2003), pp. E608-E612.
Jessop et al., "Recent Advances in the Homogeneous Hydrogenation of Carbon Dioxide", Coordination Chem. Rev. J48 (2004), pp. 2425-2442.
Koleli et al., "Reduction of CO2 Under High Pressure and High Temperature on Pb-Granule Electrodes in a Fixed-Bed Reactor in Aqueous Medium", Applied Catalysis A: General 274 (2004), pp. 237-242.
Maillard et al., "Size Effects on Reactivity of Pt Nanoparticles in CO Monolayer Oxidation: The Role of Surface Mobility", Faraday Discussions 125 (2004), pp. 357-377.
Ogura et al., "Selective Formation of Ethylene from CO2 by Catalytic Electrolysis at a Three-Phase Interface", Catalysis Today 98 (2004), pp. 515-521.
Ramirez et al., "A Supramolecular Cobalt-Porphyrin-modified Electrode, toward the Electroreduction of CO2", J. Coordination Chem. 57 (2004), pp. 249-255.
Scibioh et al., "Electrochemical Reduction of Carbon Dioxide: A Status Report", Indian Natn. Sci. Acad. 70 (2004), pp. 407-462.
Star et al., "Nanoelectronic Carbon Dioxide Sensors", Advanced Materials 16 (2004), pp. 2049-2052.
Yano et al., "Selective Electrochemical Reduction of CO2 to Ethylene at a Three-Phase Interface on Copper(I) Halide-Confined Cu-Mesh Electrodes in Acidic Solutions of Potassium Halides", J. Electroanalytical Chem. 565 (2004), pp. 287-293.
Zhao et al., "Electrochemical Reduction of Supercritical Carbon Dioxide in Ionic Liquid 1-N-Butyl-3-Methylimidazolium Hexafluorophosphate", The J. Supercritical Fluids 32 (2004), pp. 287-291.
Arenz et al., "The Effect of the Particle Size on the Kinetics of CO Electrooxidation on High Surface Area Pt Catalysts", J. Am. Chem. Soc. 127 (2005), pp. 6819-6829.
Dube et al., "Influence of Adsorption Processes on the CO2 Electroreduction, an Electrochemical Mass Spectrometry Study", J. Electroanalytical Chem. 582 (2005), pp. 230-240.
Laitar et al., "Efficient Homogeneous Catalysis in the Reduction of CO2 to CO", J. Am. Chem. Soc. 127 (2005), pp. 17196-17197.
Maillard et al., "Influence of Particle Agglomeration on the Catalytic Activity of Carbon-Supported Pt Nanoparticles in CO Monolayer Oxidation", Phys. Chem. Chem. Phys. 7 (2005), pp. 385-393.
Narayanan et al., "Catalysis with Transition Metal Nanoparticles in Colloidal Solution: Nanoparticle Shape Dependence and Stability", J. Phys. Chem. B 109 (2005), pp. 12663-12676.
Ogura et al., "Reduction of CO2 to Ethylene at Three-Phase Interface Effects of Electrode Substrate and Catalytic Coating", J. Electrochem. Soc. 152 (2005), pp. 0213-0219.
Perez et al., "In Situ FT-IR and Ex Situ EPR Analysis for the Study of the Electroreduction of Carbon Dioxide in N, NDimethylformamide on a Gold Interface", J. Electroanalytical Chem. 578 (2005), pp. 87-94.
Qu et al., "Electrochemical Reduction of CO2 on Ru02/Ti02 Nanolubes Composite Modified PI Electrode", Electrochimica Acta 50 (2005), pp. 3576-3580.
Rodriguez et al., "Specific Surface Reactions for Identification of Platinum Surface Domains: Surface Characterization and Electrocatalytic Tests", Electrochimica Acta 50 (2005), pp. 4308-4317.
Smolinka et al., "CO2 Reduction on Pt Electrocalalysts and its Impact on H2 Oxidation in CO2 Containing Fuel Cell Feed Gas—A Combined in Situ Infrared Spectroscopy, Mass Spectrometry and Fuel Cell Performance Study", Electrochimica Acta 50 (2005), pp. 5189-5199.
Blizanac et al., "Oxygen Reduction on Silver Low-Index Single-Crystal in Alkaline Solution: Rotating Ring Disk Ag (hkl) Studies", J. Phys. Chem. 110 (2006), pp. 4735-4741.
Dubois in A. Bard, ed, Encyclopedia of Electrochem., 7a, pp. 202-225. Springer (2006).

Gattrell et al., "A Review of the Aqueous Electrochemical Reduction of CO2 to Hydrocarbons at Copper", J. Electroanalytical Chem. 594 (2006), pp. 1-19.
Kaneco et al., "Electrochemical Reduction of CO2 in Copper Particle-Suspended Methanol", Chem. Eng. J. 119 (2006), pp. 107-112.
Kaneco et al., "Electrochemical Reduction of Carbon Dioxide to Ethylene at a Copper Electrode in Methanol Using Potassium Hydroxide and Rubidium Hydroxide Supporting Electrolytes", Electrochimica Acta 51 (2006), pp. 3316-3321.
Kaneco et al., "Electrochemical Reduction of CO2 to Methane at the Cu Electrode in Methanol with Sodium Supporting Salts and Its Comparison with Other Alkaline Salts", Energy & Fuels 20 (2006), pp. 409-414.
Li et al., "Development of a Continuous Reactor for the Electro-Reduction of Carbon Dioxide to Formate—Part 1: Process Variables", J. Applied Electrochem. 36 (2006), pp. 1105-1115.
Raebiger et al., "Electrochemical Reduction of CO2 to CO Catalyzed by a Bimetallic Palladium Complex Organometallics", 25 (2006), pp. 3345-3351.
Silvester et al., "Electrochem in Room Temperature Ionic Liquids: A Review and Some Possible Applications", Z. Phys. Chem. 220 (2006), pp. 1247-1274.
Solla-Gullon et al., "CO Monolayer Oxidation on Semi-Spherical and Preferentially Oriented (100) and (111) Platinum Nanoparticles", Electrochem. Communications 8 (2006), pp. 189-194.
Yano et al., "Particle-Size Effect of Nanoscale Platinum Catalysts in Oxygen Reduction Reaction: An Electrochemical and 195Pt EC-NMR Study", Phys. Chem. Chem. Phys. 8 (2006), pp. 4932-4939.
Yano, "Selective Ethylene Formation by Pulse-Mode Electrochemical Reduction of Carbon Dioxide Using Copper and Copper-Oxide Electrodes". J.Solid State Electrochem. 11 (2006), pp. 554-557.
Zhou et al., "Size Effects in Electronic and Catalytic Properties of Unsupported Palladium Nanoparticles in Electrooxidation of Formic Acid", J. Phys. Chem. B 110 (2006), pp. 13393-13398.
Zhu et al., "Supported Choline Chloride/Urea as a Heterogeneous Catalyst for Chemical Fixation of Carbon Dioxide to cyclic Carbonates", Green Chem. 9 (2006), pp. 169-172.
Begum et al., "Electrocatalysis of CO2 Reduction by Ruthenium Benzothiazole and Bithiazole Complexes", Electrochem. Communications 9 (2007), pp. 2525-2528.
Bell, "Basic Research Needs: Catalysis for Energy", U.S. Department of Energy Report PNNL-17214 (2007), p. 59.
Dubois, "Electrochemical Reactions of Carbon Dioxide", Encyclopedia of Electrochem. (2007), p. 212.
Gattrell et al., "Electrochemical Reduction of CO2 to Hydrocarbons to Store Renewable Electrical Energy and Upgrade Biogas", Energy Convers. and Manage. 48 (2007), pp. 1255-1265.
Himeda, "Conversion of CO2 into Formate by Homogeneously Catalyzed Hydrogenation in Water: Tuning Catalytic Activity and Water Solubility Through the Acid-Base Equilibrium of the Ligand", European J. Inorganic Chem. (2007), pp. 3927-3941.
Jitaru, "Electrochemical Carbon Dioxide Reduction—Fundamental and Applied Topics (Review)", J. U. of Chem. Tech. and Metallurgy 42 (2007), pp. 333-344.
Kaneco et al., "Effect of Sodium Cation on the Electrochemical Reduction of CO2 at a Copper Electrode in Methanol", J. Solid State Electrochem. 11 (2007), pp. 490-495.
Lee et al., "Studies on Suppression of Hydrogen Evolution Reaction for Zinc,/Air Fuel Cell", Material Sci. Forums 539-543 (2007), pp. 1427-1430.
Li et al., "Development of a Continuous Reactor for the Electro-Reduction of Carbon Dioxide to Formate—Part 2: Scale-Up", J. Applied Electrochem. 37 (2007), pp. 1107-1117.
Lukaszewski et al., "Comparative EQCM Study on Electrooxidation of Carbon Oxides Adsorption Products on Noble Metals and their Alloys. Polycrystalline Pd-Based Systems", J. Electroanalytical Chem. 606 (2007), pp. 117-133.
Subramanian et al. "Electrochemical Membrane Reactor for the Reduction of Carbon Dioxide to Formate", J. Applied Electrochem. 37 (2007), pp. 255-260.

(56) References Cited

OTHER PUBLICATIONS

Tian et al., "Synthesis of Tetrahexahedral Platinum Nanocrystals with High-Index Facets and High Electra-Oxidation Activity", Science 316 (2007), pp. 732-735.
PCT/US2017/025630, International Search Report and Written Opinion dated June 22, 2017 ("20170622ISR").
U.S. Appl. No. 13/445,887, Office Action dated Mar. 11, 2014 ("20140311USOA"), Office Action dated Jul. 1, 2014 ("20140701USOA"), Office Action dated Nov. 14, 2014 ("20141114USOA").
U.S. Appl. No. 15/724,933, filed Oct. 4, 2017, Office Action dated Jun. 6, 2018 ("20180606USOAb"), Office Action dated Aug. 6, 2018 ("20180806USOA").
PCT/US2011/030098, International Search Report and Written Opinion dated Jul. 6, 2011 ("20110706ISR"), International Preliminary Report on Patentability dated Jan. 3, 2013 ("20130103IPRPa").
U.S. Appl. No. 12/830,338, Third Party Submission submitted under 37 CFR 1.290 on Sep. 17 and 18, 2013 ("201309173rd Party"), Office Action dated Apr. 25, 2014 ("20140425USOA"), Office Action dated Feb. 2, 2015 ("20160202USOA"), Office Action dated Jul. 21, 2015 ("20150721USOA").
U.S. Appl. No. 13/626,873, Office Action dated Sep. 23, 2013 ("20130923USOA"), Office Action dated May 20, 2014 ("20140520USOA").
U.S. Appl. No. 14/592,246, Office Action dated Mar. 29, 2017 ("20170329USOA"), Office Action dated Nov. 27, 2017 ("20171127USOA").
U.S. Appl. No. 14/591,902, Office Action dated Feb. 2, 2016 ("20160202USOA").
U.S. Appl. No. 15/226,894, Office Action dated May 26, 2017 ("20170526USOA").
AU App. No. 2011230545, Patent Examination Report No. 1 dated Dec. 12, 2014 (20141212AUOA).
CA App. No. 2,794,105, Office Action dated Apr. 25, 2016 ("20160425CAOA"), Office Action dated Jun. 8, 2017 ("20170608CAOA").
CN App. No. 201180023851.2, Office Action dated Aug. 5, 2014 ("20140805 CNOA"), Office Action dated Oct. 16, 2015 ("20151016CNOAa").
EP App. No. 11713569.9, Office Action dated Mar. 31, 2017 ("20170331EPOA").
JP App. No. 2013-501536, Office Action dated Jan. 27, 2015 ("20150127JPOA").
JP App. No. 2015-232576, Office Action dated Dec. 20, 2016 ("20161220JPOA").
KR App. No. 10-2012-7027866, Office Action dated Aug. 1, 2016 ("20160801KROA").
PCT/US2011/042809, International Search Report and Written Opinion dated Oct. 31, 2011 ("2011103IISR"), International Preliminary Report on Patentability dated Jan, 3, 2013 ("20130103IPRPb").
U.S. Appl. No. 13/174,365, Office Action dated Apr. 8, 2015 ("20110425USOA"), Office Action dated Nov. 23, 2015 ("20151 123USOA"), Office Action dated May 16, 2016 ("20160516USOA").
AU App. No. 2011276362, Patent Examination Report No. 1 dated Nov. 5, 2014 ("20141105AUOA"), Notice of Allowance dated Mar. 2, 2016 ("20160302AUOA").
CA App. No. 2,802,893, Office Action dated May 25, 2017 ("20170525USOA").
CN App. No. 2011800331615, Office Action dated Dec. 22, 2014 (20141222CNOA), Office Action dated Oct. 16, 2015 ("20151016CNOAb"), Notification of Grant dated Jun. 14, 2016 ("20160614CNNOG").
IN Application No. 733/CHENP/2013, Examination Report dated Feb. 27, 2018 ("20180227INER").
JP App. No. 2013-5123759, Office Action dated Jun. 2, 2015 ("20150602JPOA"), Office Action dated Feb. 16, 2016 ("20160216JPOA").
JP. Application No. 2016-2323639, Office Action dated Jan. 30, 2018 ("20180130JPOA").
EP App. No 117433896, Office Action dated Apr. 5, 2017 ("20170405EPOA").
KR App. No. 10-2013-7002749, Office Action dated May 29, 2017 ("20170529KROA").
U.S. Appl. No. 13/530,058, Office Action dated Feb. 9, 2016 ("20160209USOA"), Advisory Action dated May 6, 2016 ("20160506USOA").
U.S. Appl. No. 15/148,690 0 Office Action dated Nov. 14, 2016 ("20161114USOA"), Office Action dated Mar. 21, 2017 ("20170321USOA").
AU App. No. 2016200673, Patent Examination Report No. 1 dated Aug. 2, 2016 ("20160802AUOA"), Patent Examination Report No. 2 dated Jul. 21, 2017 ("20170721AUOA").
AU App. No. 2012272770, Patent Examination Report No. 1 dated Feb. 3, 2015 ("20150203AUOA"), Patent Examination Report No. 2 dated Jan. 8, 2016 ("20160108AUOA"), Patent Examination Report No. 3 dated Jan. 28, 2016 ("20160128AUOA").
PCT/US2013/061506, International Search Report and Written Opinion dated May 16, 2014 ("20140516ISR").
PCT/US2014/018067, International Search Report and Written Opinion dated Jun. 17, 2014 ("20140617ISR").
PCT/US2015/014328, International Search Report and Written Opinion dated Jul. 6, 2015 ("20150706ISR").
PCT/US2015/026507, International Search Report and Written Opinion dated Jul. 20, 2015 ("20150720ISR").
U.S. Appl. No. 14/704,934, Office Action dated Dec. 1, 2015 ("20151201USOA"), Office Action dated Apr. 27, 2016 ("20160427USOA").
U.S. Appl. No. 14/704,935, Office Action dated Oct. 26, 2015 ("20151026USOA").
U.S. Appl. No. 15/090,477, Notice of Allowance dated Oct. 24, 2016 ("20161024USOA").
U.S. Appl. No. 15/158,227, Office Action dated Mar. 22, 2017 ("20170322USOA"), Office Action dated Sep. 22, 2017 ("20170922USOA"), Notice of Allowance dated Jan. 31, 2018 ("20180131USOA").
Sabatier et al., "Chimie Organique.—Sur la Decomposition Catalytique de I 'acide Formique", Comptes Rendus Hebdomadaires Des Seances De L'Academie Dessciences 152 (1911), pp. 1212-1215.
Popic et al., "Reduction of Carbon Dioxide on Ruthenium Oxide and Modified Ruthenium Oxide Electrodes in 0.5 M NaHCO3", J. Electroanalytical Chem. 421 (1997), pp. 105-110.
Sung et al., "Structure of Chemisorbed Sulfur on a Pl(III) Electrode", J. Am. Chem. Soc. 119 (1997), pp. 194-200.
Cherstiouk et al., "Model Approach to Evaluate Particle Size Effects in Electrocalalysis: Preparation and Properties of Pl Nanoparticles Supported on GC and HOPG", Electrochimica Acta 48 (2003), pp. 3851-3860.
Qu et al., "Electrochemical Reduction of CO2 on $RuO_2/TiO_2$ Nanolubes Composite Modified Pl Electrode", Electrochimica Acta 50 (2005), pp. 3576-3580.
Gattrell et al., "Electrochemical Reduction of CO2 to Hydrocarbons to Store Renewable Electrical Energy and Upgrade Biogas", Energy Conyers. and Manage. 48 (2007), pp. 1255-1265.
Tian et al., "Synthesis of Tetrahexahedral Platinum Nanocrystals with High-Index Facets and High Electro-Oxidation Activity", Science 316 (2007), pp. 732-735.
Xu et al., "Effects of Imidazolium Salts as Cocatalysts on the Copolymerization of CO2 with Epoxides Catalyzed by Salen) $Cr^{III}Cl$ Complex", Polymer 48 (2007), pp. 3921-3924.
Kinge et al., "Dependence of CO Oxidation on Pl Nanoparticle Shape: A Shape-Selective Approach to the Synthesis of PEMFC Catalysts", Applied Organometallic Chem. 22 (2008), pp. 49-54.
Solla-Gullon et al., "Shape-Dependent Electrocatalysis: Methanol and Formic Acid Electrooxidation on Preferentially Oriented Pl Nanoparticles", Phys. Chem. Chem. Phys. 10 (2008), pp. 3689-3698.
Cheung et al., "Electrocatalytic Reduction of Carbon Dioxide by a Polymeric Film of Rhenium Tricarbonyl Dipyridylamine", J. Organometallic Chem. 694 (2009), pp. 2842-2845.

(56) References Cited

OTHER PUBLICATIONS

Liu et al., "Observation of Surface Structural Changes of P1 Octahedron Nanoparticles and its Effect in Electrocatalyst Oxidation of Methanol", Catalysis Communications 10 (2009), pp. 1244-1247.
Chen et al., "Role of Surface Defect Sites: From Pt Model Surfaces to Shape-Controlled Nanoparticles", Chem. Sci. 3 2012), pp. 136-147.
Third-Party Submissions Under 37 CFR 1.290, submitted on Sep. 17 and 18, 2013, in connection with co-owned 6 U.S. Appl. No. 12/830,338, and Concise Description of Relevance for each of the references cited in the Third Party Submissions.
Patent Examination Report No. 2 dated Jul. 21, 2017 in connection with Australian Application No. 2016200673.
Notice of Allowance dated Feb. 21, 2019 issued in connection with Australian application No. 2017246207.
Office Action dated Feb. 26, 2019 issued in connection with Japanese application No. 2018-551990.
Office Action dated Mar. 12, 2019 issued in connection with Japanese application No. 2018-551973.
Office Action dated Mar. 21, 2019 issued in connection with Chinese application No. 201680084124.X.
Office Action dated Apr. 10, 2019 in connection with European Application No. 11743389.6-1360.
Office Action dated Jun. 17, 2019 issued in connection with Chinese application No. 201580015121.6.
Decision to Grant dated Jul. 2, 2019 issued in connection with Japanese application No. 2018-551990.
Hearing Notice dated Jul. 23, 2019 issued in connection with Indian App. No. 733/CHENP/2013.
Office Action dated Jul. 24, 2019 issued in connection with Indian application No. 201847018500.
Decision to Grant dated Aug. 6, 2019 issued in connection with Japanese application No. 2018-551973.
Office Action dated Aug. 16, 2019 issued in connection with Chinese application No. 201680084124.X.
Patent Examination Report No. 1 dated Aug. 28, 2019 issued in connection with Australian application No. 2018204762.
Office Action dated Sep. 13, 2019 issued in connection with European application No. 17720603.4.
Office Action dated Sep. 18, 2019 issued in connection with European application No. 15722607.7.
Office Action dated Sep. 18, 2019 issued in connection with European application No. 16782111.5.
Office Action dated Oct. 31, 2019 issued in connection with Indian application No. 201847020944.
Notice of Allowance dated Nov. 7, 2019 issued in connection with Australian App. No. 2018204762.
Office Action dated Dec. 10, 2019 issued in connection with Chinese application No. 201580015121.6.

* cited by examiner

ELECTROCATALYTIC PROCESS FOR CARBON DIOXIDE CONVERSION

CROSS-REFERENCE TO RELATED APPLICATIONS

This application is a continuation-in-part of U.S. patent application Ser. No. 15/724,933 filed on Oct. 4, 2017 (scheduled to issue as U.S. Pat. No. 10,173,169 on Jan. 8, 2019), entitled "Electrocatalytic Process for Carbon Dioxide Conversion". The '933 application is, in turn, a continuation-in-part of U.S. patent application Ser. No. 15/400,712 filed on Jan. 6, 2017 (now U.S. Pat. No. 9,815,021 issued on Nov. 14, 2017), also entitled "Electrocatalytic Process for Carbon Dioxide Conversion". The '712 application is, in turn, a continuation-in-part of U.S. patent application Ser. No. 14/684,145 filed on Apr. 10, 2015 (now U.S. Pat. No. 9,555,367 issued Jan. 31, 2017), also entitled "Electrocatalytic Process for Carbon Dioxide Conversion". The '712 application is also a continuation-in-part of U.S. patent application Ser. No. 15/158,227 filed on May 18, 2016 (now U.S. Pat. No. 9,945,040 issued on Apr. 17, 2018), entitled "Catalyst Layers and Electrolyzers". The '145 application is, in turn, a division of U.S. patent application Ser. No. 13/445,887 filed on Apr. 12, 2012 (now U.S. Pat. No. 9,012,345 issued on Apr. 21, 2015), entitled "Electrocatalysts for Carbon Dioxide Conversion". The '887 application is, in turn, a continuation-in-part of U.S. patent application Ser. No. 12/830,338 filed on Jul. 4, 2010, entitled "Novel Catalyst Mixtures". The '338 application claims priority benefits from U.S. provisional patent application Ser. No. 61/317,955 filed on Mar. 26, 2010, also entitled "Novel Catalyst Mixtures". The '887 application also claims priority benefits from U.S. provisional patent application Ser. Nos. 61/499,225 filed on Jun. 21, 2011, and 61/540,044 filed on Sep. 28, 2011.

The '933 application is also a continuation-in-part of the '227 application. The '227 application is, in turn, a continuation-in-part of U.S. patent application Ser. No. 14/704,934 filed on May 5, 2015 (now U.S. Pat. No. 9,481,939 issued on Nov. 1, 2016), entitled "Electrochemical Device for Converting Carbon Dioxide to a Reaction Product". The '934 application is, in turn, a continuation-in-part of international application No. PCT/US2015/14328 filed on Feb. 3, 2015, entitled "Electrolyzer and Membranes". The '328 international application claims priority benefits, in turn, from U.S. provisional patent application Ser. No. 62/066,823 filed on Oct. 21, 2014. The '934 application is also a continuation-in-part of international application No. PCT/US2015/26507 filed on Apr. 17, 2015, entitled "Electrolyzer and Membranes". The '507 international application is also a continuation-in-part of the '328 international application and also claims priority benefits from the '823 provisional application.

The '227 application is also a continuation-in-part of U.S. patent application Ser. No. 14/704,935 filed on May 5, 2015 (now U.S. Pat. No. 9,370,773 issued on Jun. 21, 2016), entitled "Ion-Conducting Membranes". The '935 application is, in turn, a continuation-in-part of the '328 international application and is also a continuation-in-part of the '507 international application.

The '227 application is also a continuation-in part of the '507 international application and is also a continuation-in-part of the '328 international application.

The '227 application also claims priority benefits from the '823 provisional application.

The '227 application is also a continuation-in-part of U.S. patent application Ser. No. 15/090,477 filed on Apr. 4, 2016 (now U.S. Pat. No. 9,580,824 issued on Feb. 28, 2017), entitled "Ion-Conducting Membranes". The '477 application is, in turn, a continuation-in-part of the '935 application.

Each of the above-identified priority applications is hereby incorporated by reference herein in its entirety.

This application is also related to international application No. PCT/US2011/042809 filed Mar. 25, 2011, entitled "Novel Catalyst Mixtures", which claims priority benefits from the '338 application, the '098 international application, U.S. provisional patent application Ser. No. 61/484,072 filed May 9, 2011, and U.S. patent application Ser. No. 13/174,365 filed Jun. 30, 2011, all entitled "Novel Catalyst Mixtures". This application is also related to U.S. provisional patent application Ser. No. 61/499,225 filed on Jun. 29, 2011, entitled "Low Cost Carbon Dioxide Sensors", and U.S. provisional patent application Ser. No. 61/540,044 filed on Sep. 28, 2011, entitled "On Demand Carbon Monoxide Generator for Therapeutic and Other Applications".

FIELD OF THE INVENTION

The field of the invention is electrocatalysis and electrocatalysts. The catalysts of this invention are applicable, for example, to the electrochemical conversion of carbon dioxide into useful products.

BACKGROUND OF THE INVENTION

There is a present need to decrease carbon dioxide ($CO_2$) emissions from industrial facilities. Over the years, a number of electrochemical processes have been suggested for the conversion of $CO_2$ into useful products. Processes for $CO_2$ conversion and the catalysts for them are discussed in U.S. Pat. Nos. 3,959,094, 4,240,882, 4,523,981, 4,545,872, 4,595,465, 4,608,132, 4,608,133, 4,609,440, 4,609,441, 4,609,451, 4,620,906, 4,668,349, 4,673,473, 4,711,708, 4,756,807, 4,818,353, 5,064,733, 5,284,563, 5,382,332, 5,457,079, 5,709,789, 5,928,806, 5,952,540, 6,024,855, 6,660,680, 6,987,134, 7,157,404, 7,378,561, 7,479,570, U.S. Patent Application Publication No. 2008/0223727 and papers reviewed by Hori (Modern Aspects of Electrochemistry, 42, 89-189, 2008) ("the Hori Review"), Gattrell, et al. (Journal of Electroanalytical Chemistry, 594, 1-19, 2006) ("the Gattrell review"), DuBois (Encyclopedia of Electrochemistry, 7a, 202-225, 2006) ("the DuBois review").

Generally, an electrochemical cell contains an anode 50, a cathode 51 and an electrolyte 53 as illustrated in FIG. 1. Catalysts are placed on the anode, and/or the cathode, and/or in the electrolyte to promote desired chemical reactions. During operation, reactants or a solution containing reactants is fed into the cell. Then a voltage is applied between the anode and the cathode, to promote an electrochemical reaction.

When an electrochemical cell is used as a $CO_2$ conversion system, a reactant comprising $CO_2$, carbonate or bicarbonate is fed into the cell. A voltage is applied to the cell, and the $CO_2$ reacts to form new chemical compounds. Examples of cathode reactions in the Hori Review include:

$CO_2 + 2e^- + 2H^+ \rightarrow CO + H_2O$ $2CO_2 + 2e^- \rightarrow CO + CO_3^{2-}$ $CO_2 + H_2O + 2e^- \rightarrow CO + 2OH^-$ $CO_2 + 2H_2O + 4e^- \rightarrow HCO^- + 3OH^-$ $CO_2 + 2H_2O + 2e^- \rightarrow H_2CO + 2OH^-$ $CO_2 + H_2O 2e^- \rightarrow (HCO_2)^- + OH^-$ $CO_2 + 2H_2O + 2e^- \rightarrow H_2CO_2 + 2OH^-$ $CO_2+5H_2O+6e^-\rightarrow CH_3OH+6OH^-$
$CO_2+6H_2O+8e^-\rightarrow CH_4+8OH^-$
$2CO_2+8H_2O+12e^-\rightarrow C_2H_4+12OH^-$
$2CO_2+9H_2O+12e^-\rightarrow CH_3CH_2OH+12OH^-$
$2CO_2+6H_2O+8e^-\rightarrow CH_3COOH+8OH^-$
$2CO_2+5H_2O+8e^-\rightarrow CH_3COO^{-}+7OH^-$
$2CO_2+10H_2O+14e^-\rightarrow C_2H_6+14OH^-$
$CO_2+2H^++2e^-\rightarrow CO+H_2O$, acetic acid, oxalic acid, oxylate
$CO_2+4H^++4e^-\rightarrow CH_4+O_2$ where $_e^-$ is an electron. The examples given above are merely illustrative and are not meant to be an exhaustive list of all possible cathode reactions.

Examples of reactions on the anode mentioned in the Hori Review include:
$2O^{2-}\rightarrow O_2+4e^-$
$2CO_3^{2-}\rightarrow O_2+2CO_2+4e^-$
$4OH^-\rightarrow O_2+2H_2O+4e^-$
$2H_2O\rightarrow O_2+4H^++4e^-$
The examples given above are merely illustrative and are not meant to be an exhaustive list of all possible anode reactions.

In the previous literature, catalysts comprising one or more of V, Cr, Mn, Fe, Co, Ni, Cu, Sn, Zr, Nb, Mo, Ru, Rh, Pd, Ag, Cd, Hf, Ta, W, Re, Ir, Pt, Au, Hg, Al, Si, In, Tl, Pb, Bi, Sb, Te, U, Sm, Tb, La, Ce, and Nd have all shown activity for $CO_2$ conversion. Reviews include Hori (Modern Aspects of Electrochemistry, 42, 89-189, 2008) ("the Hori Review"), Gattrell, et al. (Journal of Electroanalytical Chemistry, 594, 1-19, 2006) ("the Gattrell review"), DuBois (Encyclopedia of Electrochemistry, 7a, 202-225, 2006) ("the DuBois review"), and the papers Li, et al. (Journal of Applied Electrochemistry, 36, 1105-1115, 2006, Li, et al. (Journal of Applied Electrochemistry, 37, 1107-1117, 2007, and Oloman, et al. (ChemSusChem, 1, 385-391, 2008) ("the Li and Oloman papers"), and references therein.

The results in the Hon Review show that the conversion of $CO_2$ is only mildly affected by solvent unless the solvent also acts as a reactant. Water can act like a reactant, so reactions in water are different than reactions in non-aqueous solutions. But the reactions are the same in most non-aqueous solvents, and importantly, the overpotentials are almost the same in water and in the non-aqueous solvents.

The catalysts have been in the form of either bulk materials, supported particles, collections of particles, small metal ions or organometallics. Still, according to Bell (A. Bell. Ed, Basic Research Needs, Catalysis For Energy, U.S. Department of Energy Report PNNL17712, 2008) ("the Bell Report"), "The major obstacle preventing efficient conversion of carbon dioxide into energy-bearing products is the lack of catalyst" with sufficient activity at low overpotentials and high electron conversion efficiencies.

The overpotential is associated with lost energy of the process, so the overpotential should be as low as possible. Yet, according to The Bell Report "Electron conversion efficiencies of greater than 50 percent can be obtained, but at the expense of very high overpotentials". This limitation needs to be overcome before practical processes can be obtained.

A second disadvantage of many of the catalysts is that they also have low electron conversion efficiency. Catalyst systems are considered practical where electron conversion is over 50%.

U.S. patent application Ser. Nos. 12/830,338 and 13/174,365 (published as US2012/0308903), International Application No. PCT/US2011/030098 (published as WO2011/120021) and PCT/US2011/042809 (published as WO2012/006240) disclose that a catalyst mixture containing an active metal and a Helper Catalyst could catalyze $CO_2$ conversions with low overpotential and high electron conversion efficiency. However, the catalysts disclosed in these patent applications showed a lower activity than was desired.

The patent documents identified above consider applications for $CO_2$ conversion, but the present electrocatalysts overcome limitations of other systems. For example, some commercial $CO_2$ sensors use an electrochemical reaction to detect the presence of $CO_2$. At present, these sensors require over 1-5 watts of power, which is too high for portable sensing applications.

SUMMARY OF THE INVENTION

The present process employs a novel catalyst combination that can overcome one or more of the limitations of low rates, high overpotentials and low electron conversion efficiencies (namely, selectivities), low rates for catalytic reactions and high power requirements for sensors. The catalyst combination or mixture includes at least one Catalytically Active Element in the form of supported or unsupported particles wherein the particles have an average particle size (as defined below) between about 0.6 nm and 100 nm, preferably between 0.6 nm and 40 nm, and most preferable between 0.6 nm and 10 nm. The catalyst combination also includes a Helper Polymer that can contain, for example, positively charged cyclic amine groups, such as imidazoliums or pyridiniums. The catalyst combination of a Catalytically Active Element and a Helper Polymer is useful, for example, in the cathode catalyst layer of an electrochemical cell used for conversion of $CO_2$ to various reaction products.

An electrochemical device for carrying out the foregoing process can include a stack comprising at least two electrochemical cells electrically connected in series with the anode of one cell in the stack in electrical contact with the cathode from a different cell in the stack.

Preferably, the stack includes (i) a means to provide liquid electrolyte to the anode of each of the cells, (ii) a means to provide gaseous $CO_2$ to the cathodes of each of the cells, and (iii) a membrane interposed between the anode and cathode in each of the cells.

Preferably, the minimum ion conduction path between adjacent anodes is at least 3 cm.

Preferably, the minimum ion conduction path between adjacent anodes is at least 10 times the membrane thickness, most preferably at least 100 times the membrane thickness.

The present process is not limited to catalysts for $CO_2$ conversion. In particular, catalysts that include Catalytically Active Elements and Helper Catalysts or Helper Polymers might enhance the rate of a wide variety of chemical reactions. Reaction types include: homogeneously catalyzed reactions, heterogeneously catalyzed reactions, chemical reactions in chemical plants, chemical reactions in power plants, chemical reactions in pollution control equipment and devices, chemical reactions in fuel cells, and chemical reactions in sensors. The present process includes all of these examples.

DETAILED DESCRIPTION OF ILLUSTRATIVE EMBODIMENT(S)

Figure 1:
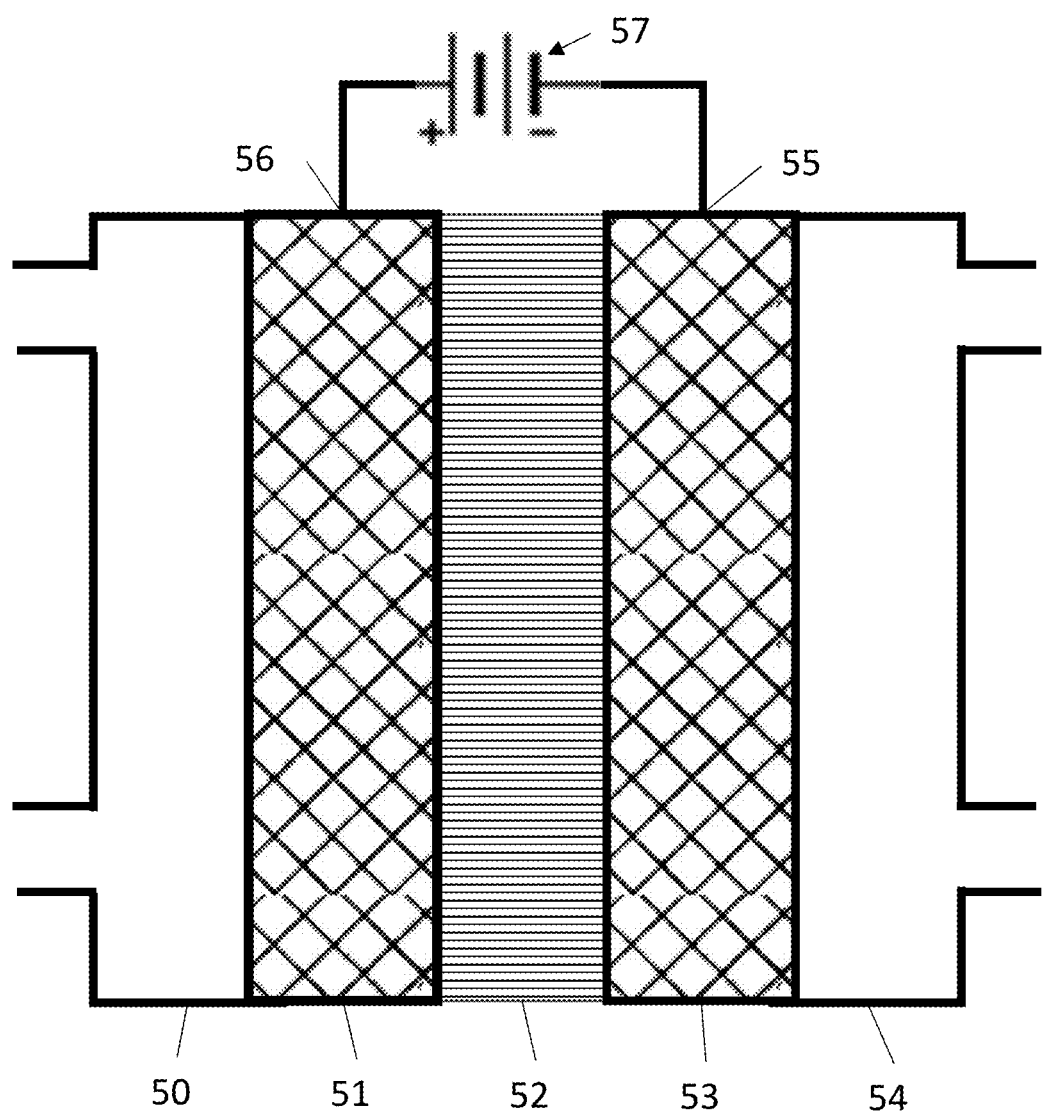
FIG. 1 is a schematic diagram of a typical electrochemical cell.

The invention disclosed herein is not limited to the particular methodology, protocols, and reagents described herein, as these can vary as persons familiar with the technology involved here will recognize. The terminology employed herein is used for the purpose of describing particular embodiments only, and is not intended to limit the scope of the invention. As used herein and in the appended claims, the singular forms "a," "an," and "the" include the plural reference unless the context clearly dictates otherwise. Thus, for example, a reference to "a linker" is a reference to one or more linkers and equivalents thereof known to persons familiar with the technology involved here.

Unless defined otherwise, all technical and scientific terms used herein have the same meanings as commonly understood by persons familiar with the technology involved here. The embodiments of the invention and the various features and advantageous details thereof are explained more fully with reference to the non-limiting embodiments and/or illustrated in the accompanying drawings and detailed in the following description, where the term "and/or" signifies either one or both of the options. It should be noted that the features illustrated in the drawings are not necessarily drawn to scale, and features of one embodiment can be employed with other embodiments as persons familiar with the technology involved here would recognize, even if not explicitly stated herein.

Any numerical value ranges recited herein include all values from the lower value to the upper value in increments of one unit provided that there is a separation of at least two units between any lower value and any higher value. As an example, if it is stated that the concentration of a component or value of a process variable such as, for example, size, angle size, pressure, time and the like, is, for example, from 1 to 90, specifically from 20 to 80, more specifically from 30 to 70, it is intended that values such as 15 to 85, 22 to 68, 43 to 51, 30 to 32, and so on, are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value are to be treated in a similar manner.

Moreover, provided immediately below is a "Definitions" section, where certain terms related to the invention are defined specifically. Particular methods, devices, and materials are described, although any methods and materials similar or equivalent to those described herein can be used in the practice or testing of the invention. All references referred to herein are incorporated by reference herein in their entirety.

Definitions

The term "electrochemical conversion of $CO_2$" as used here refers to any electrochemical process where carbon dioxide, carbonate, or bicarbonate is converted into another chemical substance in any step of the process.

The term "CV" as used here refers to a cyclic voltammogram or cyclic voltammetry.

The term "Overpotential" as used here refers to the potential difference (voltage) between a reaction's thermodynamically determined reduction or oxidation potential and the potential at which the event is experimentally observed.

The term "Cathode Overpotential" as used here refers to the overpotential on the cathode of an electrochemical cell.

The term "Anode Overpotential" as used here refers to the overpotential on the anode of an electrochemical cell.

The term "Electron Conversion Efficiency" refers to selectivity of an electrochemical reaction. More precisely, it is defined as the fraction of the current that is supplied to the cell that goes to the production of a desired product.

The term "Catalytically Active Element" as used here refers to any chemical element that can serve as a catalyst for the electrochemical conversion of $CO_2$.

The term "Helper Catalyst" as used here refers to any organic molecule or ion, or a mixture of organic molecules and/or ions, that does at least one of the following:
  (a) Speeds up a chemical reaction; or
  (b) Lowers the overpotential of the reaction,
without being substantially consumed in the process.

The term "Helper Polymer" as used here refers to a polymer that does at least one of the following:
  (a) Speeds up a chemical reaction;
  (b) Increases the current seen in an electrochemical reaction at a given potential;
  (c) Increases the Faradaic efficiency of a given reaction; or
  (d) Increases the selectivity of a reaction.

The term "MEA" as used here refers to a membrane electrode assembly.

The term "imidazolium" as used here refers to a positively charged ligand containing an imidazole group. This includes a bare imidazole or a substituted imidazole. Ligands of the form:

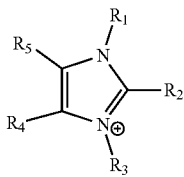

where $R_1$-$R_5$ are each independently selected from hydrogen, halogens, linear alkyls, branched alkyls, cyclic alkyls, heteroalkyls, aryls, cyclic aryls, heteroaryls, alkylaryls, heteroalkylaryls, and polymers thereof, such as the vinyl benzyl copolymers described herein, are specifically included.

The term "pyridinium" as used here refers to a positively charged ligand containing a pyridinium group. This includes a protonated bare pyridine or a substituted pyridine or pyridinium. Ligands of the form:

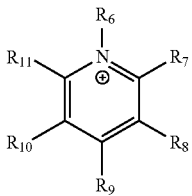

where $R_6$-$R_{11}$ are each independently selected from hydrogen, halogens, linear alkyls, branched alkyls, cyclic alkyls, heteroalkyls, aryls, cyclic aryls, heteroaryls, alkylaryls, heteroalkylaryls, and polymers thereof, such as the vinyl benzyl copolymers described herein, are specifically included.

The term "pyrazoliums" as used here refers to a positively charged ligand containing a pyrazolium group. This includes a bare pyrazolium or a substituted pyrazolium. Ligands of the form:

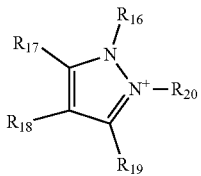

where $R_{16}$-$R_{20}$ are each independently selected from hydrogen, halogens, linear alkyls, branched alkyls, cyclic alkyls, heteroalkyls, aryls, cyclic aryls, heteroaryls, alkylaryls, heteroalkylaryls, and polymers thereof, such as the vinyl benzyl copolymers described herein, are specifically included.

The term "phosphonium" as used here refers to a positively charged ligand containing phosphorous. This includes substituted phosphorous. Ligands of the form:

$P^+(R_{12}R_{13}R_{14}R_{15})$ where $R_{12}$-$R_{15}$ are each independently selected from hydrogen, halogens, linear alkyls, branched alkyls, cyclic alkyls, heteroalkyls, aryls, cyclic aryls, heteroaryls, alkylaryls, heteroalkylaryls, and polymers thereof, such as the vinyl benzyl copolymers described herein, are specifically included.

The term "positively charged cyclic amine" as used here refers to a positively charged ligand containing a cyclic amine. This specifically includes imidazoliums, pyridiniums, pyrazoliums, pyrrolidiniums, pyrroliums, pyrimidiums, piperidiniums, indoliums, triaziniums, and polymers thereof, such as the vinyl benzyl copolymers described herein.

The term "polymer electrolyte membrane" refers to both cation exchange membranes, which generally comprise polymers having multiple covalently attached negatively charged groups, and anion exchange membranes, which generally comprise polymers having multiple covalently attached positively charged groups. Typical cation exchange membranes include proton conducting membranes, such as the perfluorosulfonic acid polymer available under the trade designation NAFION from E.I. du Pont de Nemours and Company (DuPont) of Wilmington, Del.

The term "anion exchange membrane" as used here refers to membranes comprising polymers wherein said polymers comprise positively charged groups.

The term "stack" as used here refers to a plurality of electrochemical cells connected in series.

The term "ion conduction path" as used here is the path that ions can take from one cell to another in a stack without the ions going through the membranes separating the anode and the cathode in any cell.

SPECIFIC DESCRIPTION

The present process relates generally to Catalytically Active Element, Helper Polymer Mixtures where the mixture does at least one of the following:
(a) Speeds up a chemical reaction;
(b) Increases the current seen in an electrochemical reaction at a given potential;
(c) Increases the Faradaic efficiency of a given reaction; or
(d) Increases the selectivity of a reaction.

For example, such mixtures can increase the rate of $CO_2$ conversion to a value that is higher than when the same Catalytically Active Element is used without the Helper Polymer.

U.S. patent application Ser. Nos. 12/830,338, 13/174,365, and International Application No. PCT/US2011/030098 (published as WO2011/120021) and PCT/US2011/042809 (published as WO2012/006240) disclose that a catalyst mixture containing a Catalytically Active Metal and a Helper Catalyst catalyzes $CO_2$ conversions with low overpotential and high electron conversion efficiency. Active Metals included one or more of V, Cr, Mn, Fe, Co, Ni, Cu, Sn, Zr, Nb, Mo, Ru, Rh, Pd, Ag, Cd, Hf, Ta, W, Re, Ir, Pt, Au, Hg, Al, Si, In, Tl, Pb, Bi, Sb, Te, U, Sm, Tb, La, Ce, and Nd. Examples of Helper Polymers include polymers containing one or more of positively charged cyclic amines, phosphines, imidazoliums, pyridiniums, pyrrolidiniums, phosphoniums, sulfoniums, prolinates, methioninates, cholines, acetylcholines, alanines, aminoacetonitriles, methylammoniums, arginines, aspartic acids, threonines, chloroformamidiniums, thiourouniums, quinoliniums, pyrrolidinols, serinols, benzamidines, sulfamates, acetates, carbamates, triflates, and cyanides.

Of course, the '338 U.S. application, the '365 U.S. application, the '098 international application and the '809 international application disclose that not every substance listed above will act as a Helper Polymer. In general, one can determine whether a polymer P is a Helper Catalyst for electrochemical conversion of $CO_2$ catalyzed by a catalytically active element M by the following test:
(1) Prepare two different membrane electrode assemblies (MEAs) with 5 cm² of active area: (i) one having the polymer P in the cathode catalyst layer; and (ii) one otherwise identical but without the polymer P in the cathode catalyst layer, wherein the weight of the polymer is 4% of the weight of the catalytically active element M.
(2) Both membrane electrode assemblies are mounted in Fuel Cell Technologies (Albuquerque, N. Mex.) 5 cm² fuel cell hardware assembly with serpentine flow fields.
(3) $CO_2$ humidified at 50° C. is fed into the cathode of both cells at a rate of 5 sccm with the cell at room temperature and pressure, and the anode side is left open to the atmosphere at room temperature and pressure.
(4) A voltage of 1 V is applied to the cell without the polymer P, and then the voltage is raised to a voltage V such that the output current is as least 20 mA/cm². The current output of the cell is recorded after running for 30 minutes.
(5) The same voltage V is applied to the cell with the polymer P and the current output of the cell is recorded after running for 30 minutes.

If the current is at least 20% higher in the cell with the polymer P in the catalyst layer than the cell without the polymer P in the catalyst layer, the polymer P is a Helper Polymer for that reaction.

Preferably the two MEA's are manufactured as follows:
(1) A solvent S is identified such that S can dissolve at least 5 mg of the polymer P in 3 mL of solution.
(2) A cathode for the MEA containing the polymer P is prepared as follows:
　(a) 100 mg of nanoparticles of Catalytically Active Element M are mixed with 4 mg of polymer P, and 3 mL of solvent S.
　(b) The mixture is sonicated for 10 minutes to create a catalyst ink.
　(c) The ink is painted onto a gas diffusion layer (Sigracet 35 BC GDL, Ion Power Inc., New Castle, Del.) covering an area of 6 cm×6 cm. The electrode was immersed in 1 M KOH for at least 1 hour for ion exchange, then the electrode is cut into 2.5 cm×2.5 cm sections for cell testing.
(3) The anode for the MEA is prepared as follows:
　(a) 100 mg of $IrO_2$ (43396, Alfa Aesar, Ward Hill, Mass.) is dispersed in the mixture of 1 ml of deionized water, 2 ml of isopropanol (3032-16, Macron Fine Chemicals, Avantor Performance Materials, Center Valley, Pa.) and 0.1 ml of 5 wt. % polytetrafluoroethylene (PTFE) dispersion (665800, Sigma-Aldrich, St. Louis, Mo.).
　(b) The mixture is sonicated for 10 min using a water bath sonicator.
　(c) The ink is painted onto 6 cm×6 cm of carbon fiber paper (Toray Paper 120, Fuel Cell Earth, Woburn, Mass.). The $IrO_2$ loading is about 2 mg/cm². The electrode is cut into 3 cm×3 cm sections for cell testing.
(4) An anion exchange membrane is sandwiched between the anode and the cathode with the metal-containing layers on the anode and cathode facing the membrane to create the MEA. Preferably the anion exchange membrane is one of the helper membranes described in U.S. Pat. No. 9,370,773.
(5) The same procedure is used to create the MEA the does not contain the Polymer, except no polymer P is added in step 2a.

In the foregoing applications, new catalyst formulations are disclosed that maintain the ability to convert $CO_2$ with a high electron conversion efficiency and low overpotential, but also show an improved specific catalytic activity. The catalyst of the present application was prepared by modifying the structure of the silver so it is more active. The catalyst can be in the form of supported or unsupported metal particles wherein the average particle size is below about 100 nm, preferably between 0.6 nm and 40 nm, more preferably between 0.6 nm and 20 nm, and most preferably between 0.6 nm and 10 nm.

In this context, the particle sizes can be determined by one or more of microscopy, x-ray line broadening, chemisorption, or small angle x-ray scattering. For example, one might measure the x-ray diffraction pattern of the catalysts, determine β the width of the diffraction line at some angle θ and then calculate the particle size, D, from the Scherrer equation:

$$D = \frac{0.9\lambda}{\beta \cos(\theta)}$$

where λ is the wavelength of the x-ray beam.

Chemisorption can alternately be used to measure the $S_g$, the surface area of the active element per unit mass, and then calculate the particle size from the formula:

$$D = \frac{5}{S_g \rho}$$

where ρ is the bulk density of the active element.

The present process specifically includes any catalyst with a particle size between 0.6 nm and 100 nm measured by any of x-ray line broadening, chemisorption, or small angle x-ray scattering.

BACKGROUND DATA

An Illustration of the Effects of Particle Size on $CO_2$ Conversion on a Silver/EMIM Catalyst Catalysts Tested This example illustrates the effect of silver particle size on the rate of $CO_2$ conversion on an EMIM-BF4 (Sigma Aldrich, St. Louis, Mo.) coated silver catalyst.

Experimental Data

During the experiments, a silver ink was deposited onto a silver rotating disk electrode (Pine Instruments, Grove City, Pa.). In the first experiment, the silver electrode was polished, and a CV was run as described in the fourth paragraph below. Subsequent experiments were run by depositing one of: (i) 200 nm silver (Sigma Aldrich, St. Louis, Mo.); (ii) 100 nm silver (Sigma Aldrich); (iii) 20-40 nm silver (Sigma Aldrich); (iv) 5 nm (UT Dots, Champaign, Ill.); (v) 0.67 nm (Purest Colloids, Westampton, N.J.) onto the silver electrode and running the CV as set forth in the fourth paragraph below.

In the case of 500-1000 nm, 100 nm, and 20-40 nm silver, a silver ink was prepared by mixing 5.6 mg of silver particles with 1 ml deoxygenated Millipore water. The catalyst was applied on the surface of a rotating electrode by adding 60

µL of the ink to the surface and allowing the water to evaporate under ambient temperature for 60 minutes. In order to ensure the quality of the measurements, special attention was paid to the material cleaning and solution purity.

The 10 nm Ag arrived suspended in an organic solution, so this solution was applied to the silver electrode, and subsequently heated in air at 85° C. for 3 hours to remove residual organics.

The 0.6 nm Ag particles arrived suspended in distilled water, so they were used as received.

The counter electrode was made by attaching a 25 mm×25 mm platinum mesh (size 52) to a 5-inch platinum wire (99.9%, 0.004-inch diameter). A silver quasi-reference electrode (Ag-QRE) was used. The electrolytes were first loaded into the glass cell and then purged with dry argon (99.99%) for two hours in order to remove oxygen from the electrolytes. Prior to each experiment, a 20-40 linear sweep cyclic voltammogram at 75 mVs$^{-1}$ was taken with the range between −2 V and 0 vs.

Ag-QRE in order to condition the electrodes and remove oxides from the surfaces. Then several cycles were performed at 10 mVs$^{-1}$ before taking the final cycle to ensure that the CV had stabilized (that is, any "dirt" or other material was removed from the surfaces). Finally, cleaning and stabilizing CV cycles were performed at 10 mVs$^{-1}$. Then $CO_2$ was bubbled in the solution at 1 atm pressure for 20 minutes. Cyclic voltammetry was conducted again at a sweep rate of 10 mV/s in the range from −2 V to 0 V vs. Ag-QRE.

Results: Water Electrolysis

Figure 2:
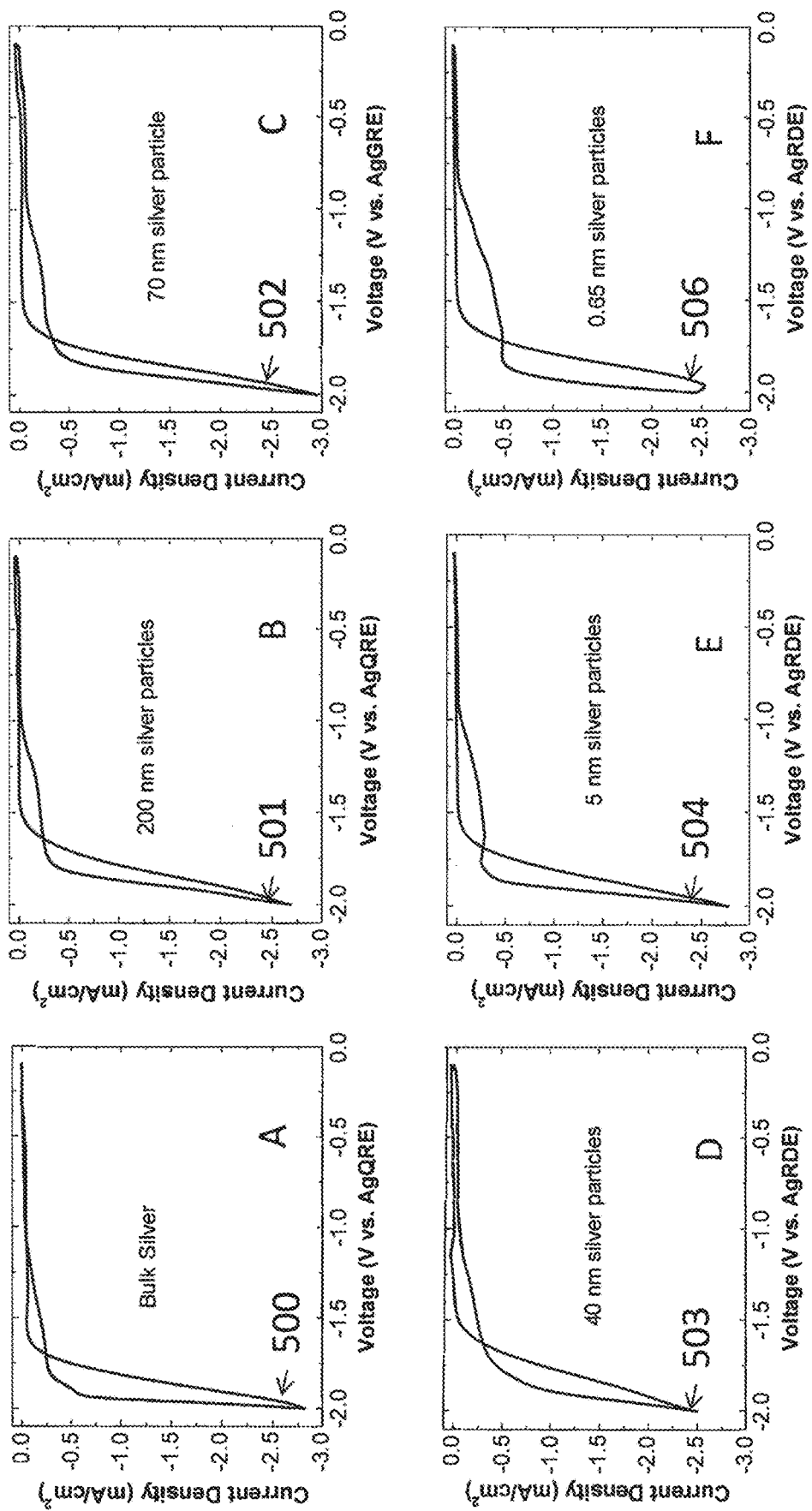
FIG. 2 illustrates how the cyclic voltammogram (CV) of electrochemical water reduction varies with the average particle size of the Catalytically Active Element silver on the cathode: (A) bare silver electrode, (B) electrode covered by nominally 200 nm silver particles, (C) electrode covered by nominally 100 nm silver particles, (D) electrode covered by nominally 20-40 nm silver particles, (E) electrode covered by 5 nm silver particles, and (F) electrode covered by 0.67 nm silver particles. The numeric designations 500-505 indicate the positions of the hydrogen peak in the figures. All of the CV's are reported as the current divided by the electrochemical surface area of the particles

FIG. 2 shows how the CV of water varies with particle size. One finds that there is very little variation in the catalytic activity of silver, in agreement with the literature reviewed in a recent paper, M.T.M. Koper, "Structural sensitivity and nanostructure effects in electrocatalysis", Nanoscale 3, 2054 (2011) ("the Koper Paper").

Results: $CO_2$ Electrolysis

Figure 3:
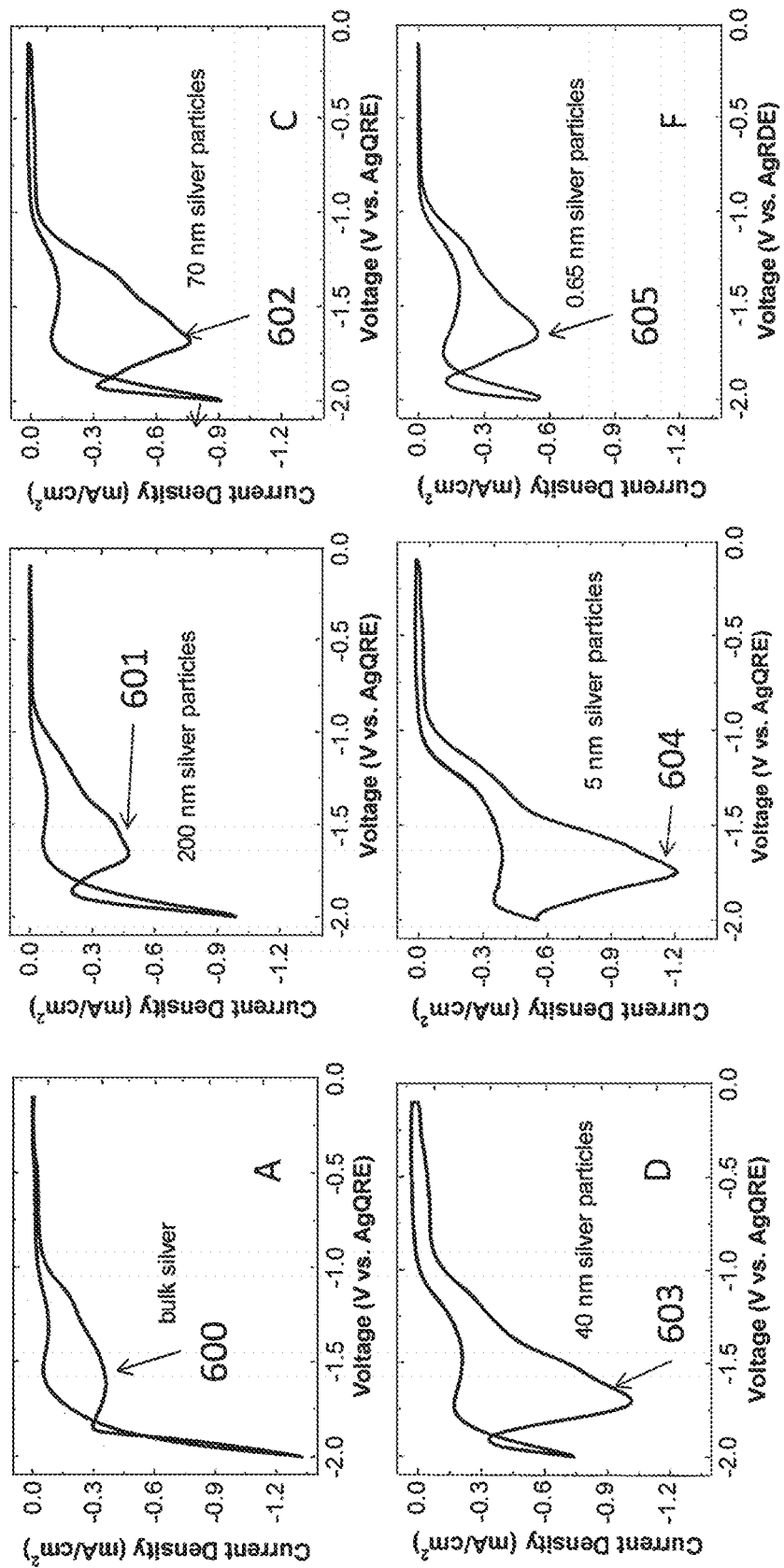
FIG. 3 illustrates how the CV changes in FIG. 2 when $CO_2$ is added to the reaction: (A) bare silver electrode, (B) electrode covered by nominally 200 nm silver particles, (C) electrode covered by nominally 100 nm silver particles, (D) electrode covered by nominally 20-40 nm silver particles, (E) electrode covered by 5 nm silver particles, and (F) electrode covered by 0.67 nm silver particles. The numeric designations 600-605 indicate the $CO_2$ reduction peak in the figures. All of the CV's are reported as the current divided by the electrochemical surface area of the particles
Figure 4:
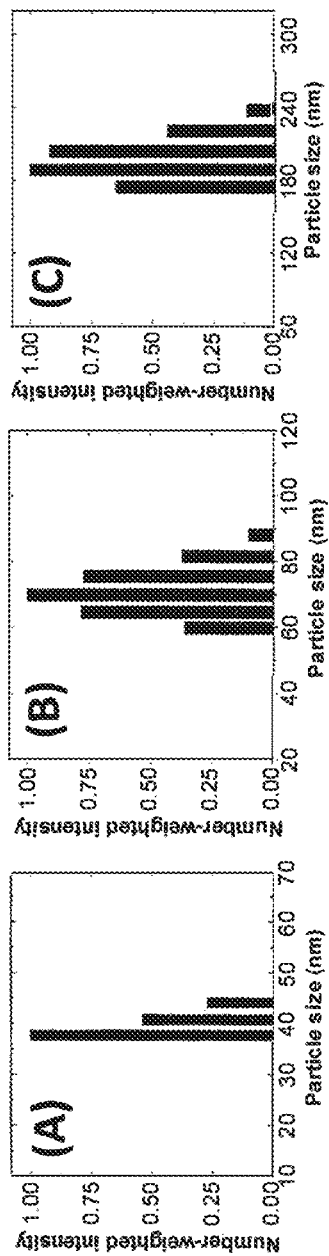
FIG. 4 illustrates particle size distribution of the (A) nominally 20-40 nm silver particles, (B) nominally 100 nm silver particles, and (C) nominally 200 nm silver particles as measured by dynamic light scattering. The nominally 20-40 nm particles have an average size of 35 nm. The nominally 100 nm particles have an average size of 70 nm and the nominally 200 nm particles have an average size of 190 nm.

FIG. 3 shows how the CV changes when $CO_2$ is added to the electrochemical cell. Notice that $CO_2$ conversion peaks, labeled 100, 101, 102, 103, 104, 105 and 106 are observed. The $CO_2$ conversion peaks grow as one decreases the particle size from 1000-10 nm, but then we observed the opposite effect, where the $CO_2$ peak shrinks moving from 10 nm to 0.6 nm. Evidently, there is an optimal particle size somewhere between 0.6 and 100 nm. The optimal size is probably between 0.6 and 40 nm, most probably between 0.6 and 20 nm.

The result above shows that unsupported silver catalysts have an optimal size between 0.6 and 100 nm. Those familiar with the technology involved here know that if a reaction is structure sensitive on an unsupported catalyst, or single crystal, it will also show structure sensitivity on a supported catalyst. Further, the Koper paper suggests that if a reaction is structure sensitive on one transition metal, it will also be structure sensitive on most other transition metals. In particular, the optimum particle size is very similar on most transition metals. Therefore, we conclude that V, Cr, Mn, Fe, Co, Ni, Cu, Zr, Nb, Mo, Ru, Rh, Pd, Ag, Cd, W, Re, Ir, Pt, Au, Hg, Pb and Bi electrocatalysts for $CO_2$ conversion should have an optimal particle size between 0.6 and 100 nm.

Example 1: Use of Solid Polymers as Helper Catalysts

The objective of this example is to show that polymers containing imidazoliums can be Helper Catalysts.

A copolymer, which is designated here as PSMIM (Cl), was prepared following the synthetic route in U.S. Pat. No. 9,370,773. "PSMIM" refers to a co-polymer of polystyrene and poly 1-(p-vinylbenzyl)-3-methyl-imidazolium:

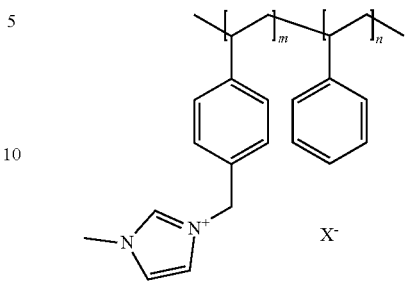

where X$^-$ is an anion, m>0 and n>0.

The inhibitor-free styrene was prepared by passing styrene (Sigma-Aldrich) through the tert-butylcatechol (TBC) inhibitor remover (Sigma-Aldrich 311340). In general, 40 ml of remover is sufficient to yield 50 ml of clear, inhibitor free styrene. Inhibitor TBC in 4-vinylbenzyl chloride (4-VBC) was removed by the same inhibitor remover in a similar fashion.

Poly(4-vinylbenzyl chloride-co-styrene) was then synthesized by heating a solution of inhibitor-free styrene (Sigma-Aldrich) (36.139 g, 350 mmol) and 4-vinylbenzyl chloride (Sigma-Aldrich) (29.7272 g, 190 mmol) in chlorobenzene (Sigma-Aldrich) (45 ml) at 60-65° C. in an oil bath for approximately 20 hours under argon gas with AIBN (α,α'-Azoisobutyronitrile, Sigma-Aldrich) (0.5927 g, 0.90 wt % based on the total monomers' weight) as initiator. The copolymer was precipitated in $CH_3OH$ (methanol) and dried under vacuum.

"4-VBC-co-St" or "poly(4-vinylbenzyl chloride co-styrene)" as used here refers to a co-polymer of styrene and 4-vinylbenzyl chloride:

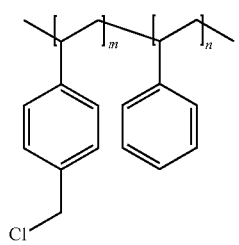

where m>0 and n>0.

"Polystyrene methyimidazolium chloride" (PSMIM-Cl) was synthesized by adding 1-methylimidazole (Sigma-Aldrich) (2.8650 g, 034.9 mmol), which is an alkylimidazole, to the solution of the poly(4-VBC-co-St) (5.0034 g, 19.4 mmol) in anhydrous N,N-Dimethylformamide (DMF) (Sigma-Aldrich) (30 mL). The mixture was then stirred at around 30° C. for around 50 hours to form a PSMIM solution.

"4-VBC-co-St" or "poly(4-vinylbenzyl chloride co-styrene)" as used here refers to a co-polymer of styrene and 4-vinylbenzyl chloride:

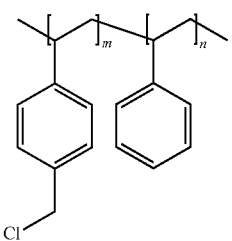

where m>0 and n>0.

Anion exchange membrane polymer PSMIM-DVB was synthesized starting with poly(4-vinylbenzyl chloride co-styrene.) 1-methylimidazole (Sigma-Aldrich) (3.912 g, 47.7 mmol) was added in a 250 ml 3-neck round bottom flask to the solution of the poly(4-VBC-co-St) (15.358 g, 59.8 mmol) in anhydrous N,N-Dimethylformamide (DMF) (Sigma-Aldrich) (105 ml). 0.22 ml of a divinylbenzene (DVB) in DMF solution (DVB concentration=0.0083 g/ml) was carefully added through a pipette to the mixture with continual magnetic stirring. After this, 0.22 ml of AIBN-DMF solution (AIBN concentration=0.0083 g/ml) was added to the mixture in a similar fashion. The reaction was then kept under nitrogen atmosphere at 50° C. for about 60 hours. PSMIM-DVB was obtained as a white powder after purification by precipitation into diethyl ether.

Membranes were prepared by casting the PSMIM-DVB solution prepared above directly onto a flat glass surface. The thickness of the solution on the glass was controlled by a film applicator (MTI Corporation, Richmond, Calif.) with an adjustable doctor blade. The membranes were then dried in a vacuum oven in the following stepwise fashion. They were first kept at 80° C. for 120 minutes, then at 100° C. for 60 minutes, at 120° C. for 30 minutes and finally at 150° C. for 60 minutes. Chloride ions in the membranes were removed by soaking the membranes in 1 M KOH solution for 24 hours or longer.

The cathode layer in Example 1 was prepared as follows. Silver ink was made by mixing 100 mg of silver nanoparticles (20-40 nm, 45509, Alfa Aesar, Ward Hill, Mass.), 5 mg porous carbon (Vulcan XC-72R, Fuel Cell Earth, Woburn, Mass.) and different amounts of PSMIM-Cl in 3 ml of ethanol (459844, Sigma-Aldrich). The mixture was then sonicated for 10 minutes. The silver ink was painted onto a gas diffusion layer (Sigracet 35 BC GDL, Ion Power Inc., New Castle, Del.) covering an area of 6 cm×6 cm. The electrode was immersed in 1 M KOH for at least 1 hour so that PSMIM-Cl converted by ion exchange to PSMIM-OH. Then the electrode was cut into 2.5 cm×2.5 cm sections for cell testing.

The anode in Example 1 was prepared as follows: 100 mg of $IrO_2$ (43396, Alfa Aesar) was dispersed in the mixture of 1 ml of deionized water, 2 ml of isopropanol (3032-16, Macron Fine Chemicals, Avantor Performance Materials, Center Valley, Pa.) and 0.1 ml of 5 wt. % poly-tetrafluoroethylene (PTFE) dispersion (665800, Sigma-Aldrich). The mixture was sonicated for 10 min using a water bath sonicator. The ink was painted onto 6 cm×6 cm of carbon fiber paper (Toray Paper 120, Fuel Cell Earth). The actual $IrO_2$ loading was about 2 mg/cm². The electrode was cut into 3 cm×3 cm sections for cell testing.

The PSMIM-DVB membrane was sandwiched between the anode and the cathode with the metal-containing layers on the anode and cathode facing the membrane, and the whole assembly was mounted in a Fuel Cell Technologies 5 cm² fuel cell hardware assembly with serpentine flow fields configured as in FIG. 1 with an anode gas chamber 50, an anode 51, a membrane 52, a cathode 53, cathode gas chamber 54, a means to make a connection with the cathode 55, a means to make a connection to the anode 56. The figure also shows a source of potential to device 57. In the experiments reported here that source was a potentiostat although many other power supplies could be used.

$CO_2$ humidified at 25° C. was fed into the cathode flow field at a rate of 20 sccm, and 10 mM $KHCO_3$ was fed into the anode flow field. The cyclic voltammograms were collected by scanning the cell voltage from 1.2 to 3.0 V. All of the scans were made at room temperature and atmospheric pressure.

Figure 5:
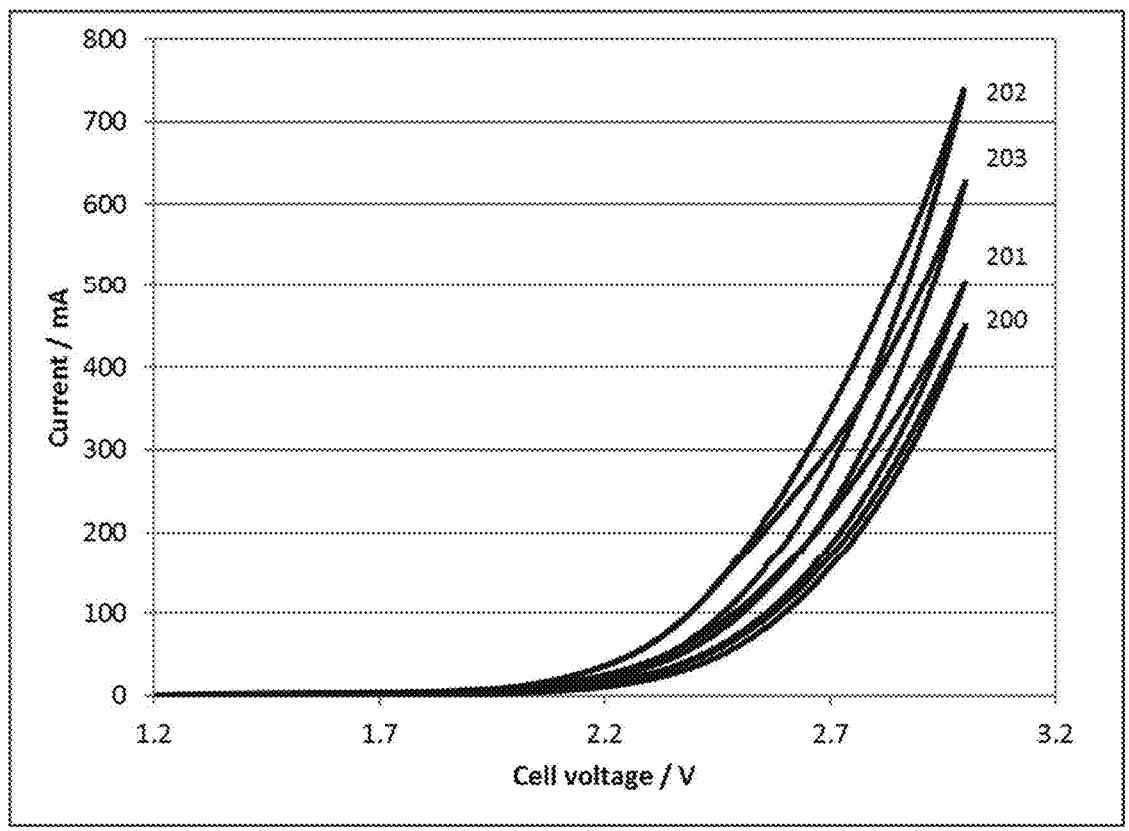
FIG. 5 shows how the voltammograms of a 5 $cm^2$ cell change when 0% (plot 200), 1% (plot 201), 5% (plot 202), and 10% (plot 203) of Helper Polymer PSMIMCl are added to the $CO_2$ electrolyzer cathode catalyst layer, where the percentage is calculated as the weight of the PSMIMCl divided by the weight of the silver. "PSMIMCl" refers to the chloride form of a co-polymer of polystyrene and poly 1-(p-vinylbenzyl)-3-methyl-imidazolium.

FIG. 5 shows the results of the above scans. Plot 200 is a base case with no PSMIM in the cathode catalyst layer ink. It should be noted that the current increases when PSMIM is added to the catalyst layer in a later sample, such that the PSMIM weight is 1% of the weight of the silver (plot 201). Further increases in the current are seen as the PSMIM concentration is increased so that the PSMIM weight is 5% of the weight of the silver (plot 202). Then there is a small decrease when the weight of the PSMIM is increased to 10% of the weight of the silver (plot 203).

A run in which the PSMIM weight was 20% of the weight of the silver was also performed. The cell showed a small current, but analysis of the exit stream did not show significant $CO_2$ conversion.

These results demonstrate that the addition of an ionomer containing an imidazolium to the cathode catalyst layer enhances the performance of a $CO_2$ electrolyzer and the PSMIM polymer is therefore a Helper Polymer.

U.S. patent application Ser. No. 15/158,227 (now U.S. Pat. No. 9,945,040) provides a number of other examples. The data in the '227 application indicates that polymers containing positively charged cyclic amines can also act as Helper Polymers.

Example 2: Stacks

Figure 6:
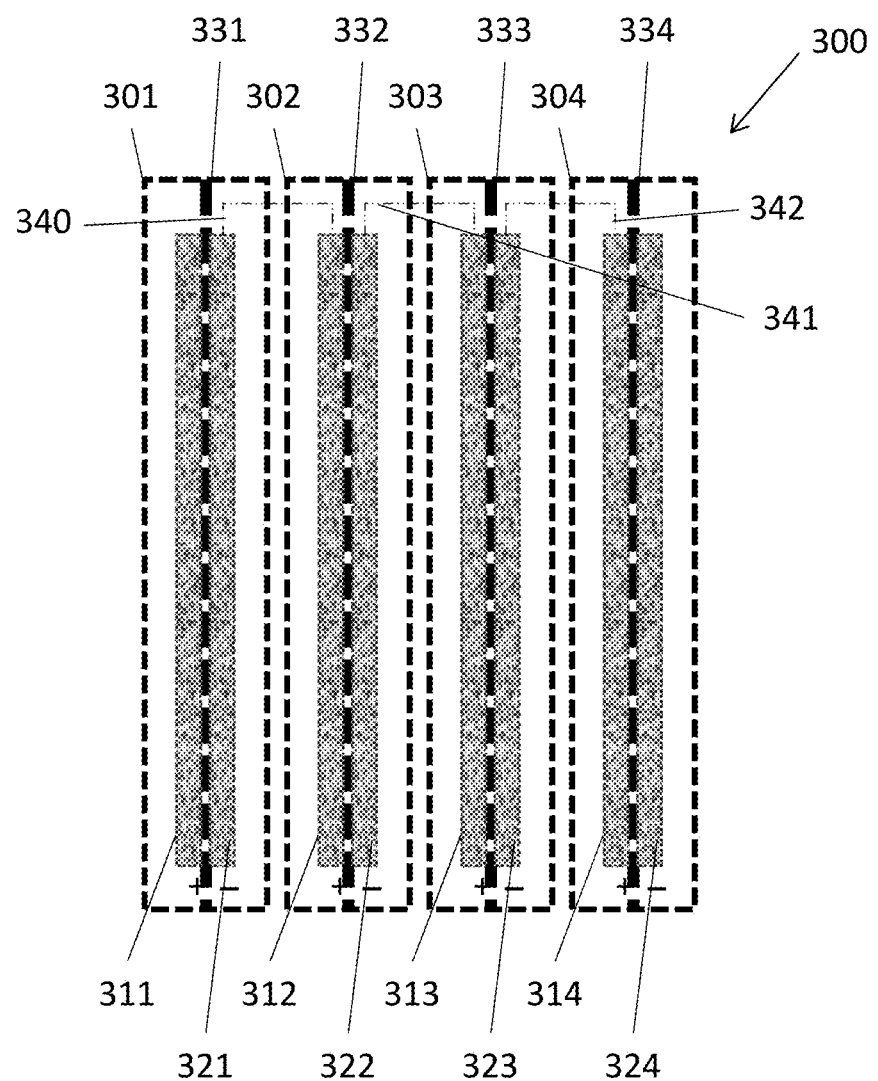
FIG. 6 illustrates an embodiment of the stacks described herein, which comprise two or more electrochemical cells, each of which consists of an anode, a cathode, a membrane interposed between the anode and the cathode, and an electrical connection between cells.

Example 1 used a single cell, but commercial designs will use a stack 300 where multiple cells are interconnected as illustrated in FIG. 6. The stack consists of a number of cells 301, 302, 303 and 304. Each cell has an anode 311, 312, 313 and 314, respectively, a cathode 321, 322, 323 and 324, respectively, and an ion-conducting membrane 331, 332, 333 and 334, respectively, interposed between the anode and the cathode. There are electrical connections 340, 341, 342 between (i) cathode 321 and anode 312, (ii) cathode 322 and anode 313, and (iii) cathode 323 and anode 314. Electrical potential is provided between anode 311 and cathode 324.

The figure only shows one example. There can be between 2 and 1000 cells in the stack.

Multiple arrangements of power are possible. In one case, power is provided to the ends of the stack. In a second case, power is provided to individual sections of the stack so that there is a source of potential between the cathode of one cell in the stack and the anode of a different cell in the stack.

The design also includes examples where the anode of one cell is in electrical contact with the cathode of an adjacent cell. The design also includes examples where the anode of one cell is in electrical contact with the cathode of a different, non-adjacent, cell in the stack.

The stack includes a means to feed gaseous $CO_2$ with negligible liquid into the cathode and means to feed a liquid electrolyte such as dilute potassium bicarbonate into the anode. This differs from conventional electrochemical stacks where either (i) liquid electrolyte is fed into both sides of the stack, (ii) gas is fed into both sides of the stack, and/or (iii) a non-conductive liquid such as deionized water is fed into one or both of the sides.

The ion conduction path between two adjacent anodes is at least 3 cm. It also is at least 10 times and preferably at least 100 times the membrane thickness.

The example given above is illustrative and is not meant to be an exhaustive list of all possible embodiments, applications or modifications of the invention. Thus, various modifications and variations of the described methods and systems of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention which are obvious to those skilled in the chemical arts or in the relevant fields are intended to be within the scope of the appended claims.

The disclosures of all references and publications cited above are expressly incorporated by reference in their entireties to the same extent as if each were incorporated by reference individually.

While particular elements, embodiments and applications of the present invention have been shown and described, it will be understood that the invention is not limited thereto since modifications can be made by those skilled in the art without departing from the scope of the present disclosure, particularly in light of the foregoing teachings.

What is claimed is:

1. An electrochemical device for converting $CO_2$ to a reaction product, the device comprising an electrolyzer stack, wherein the stack comprises at least two electrochemical cells, wherein each cell comprises:
   (a) an anode comprising a quantity of anode electrocatalyst;
   (b) a cathode comprising a quantity of cathode electrocatalyst;
   (c) a source of $CO_2$ directed to said cathode;
   (d) a membrane interposed between said anode and said cathode, wherein:
      (i) said cathode electrocatalyst is in the form of unsupported particles or particles supported on an electrically conductive support;
      (ii) said particles have an average size between 0.6 nm and 100 nm; and
      (iii) said cathode electrocatalyst converts $CO_2$ to a carbon-containing reaction product.

2. The electrochemical device of claim 1, wherein said membrane has an average thickness and the shortest ion conduction path between anodes of different cells in the stack is at least 10 times the average membrane thickness.

3. The electrochemical device of claim 2, wherein the shortest ion conduction path between anodes of different cells in the stack is at least 100 times the average membrane thickness.

4. The electrochemical device of claim 1, wherein the shortest ion conduction path between anodes of different cells in the stack is at least 3 cm.

5. The electrochemical device of claim 1, further comprising a conduit fluidly connecting the anode of one cell in the stack to the anode of a different cell in the stack, and a source of liquid electrolyte directed to said conduit.

6. The electrochemical device of claim 1, further comprising an electrical connection between the anode of one cell in the stack and the cathode of a different cell in the stack.

7. The electrochemical device of claim 6, further comprising a source of potential between the cathode of the one cell in the stack and the anode of a different cell in the stack.

8. The electrochemical device of claim 1, further comprising a conduit fluidly connecting the cathode of one cell in the stack to the cathode of a different cell in the stack, said source of $CO_2$ directed to said conduit.

9. The electrochemical device of claim 8, wherein said $CO_2$ is in gaseous form.

10. The electrochemical device of claim 1, wherein said membrane is a polymer electrolyte membrane.

11. The electrochemical device of claim 10, wherein said membrane is an anion exchange membrane.

12. The electrochemical device of claim 1, wherein the average particle size of said particles is between 0.6 nm and 40 nm.

13. The electrochemical device of claim 1, wherein said electrocatalyst comprises at least one of V, Cr, Mn, Fe, Co, Ni, Cu, Sn, Zr, Nb, Mo, Ru, Rh, Pd, Ag, Cd, Hf, Ta, W, Re, Ir, Pt, Au, Hg, Al, Si, In, Tl, Pb, Bi, Sb, Te, U, Sm, Tb, La, Ce, and Nd.

14. The electrochemical device of claim 13, wherein said Catalytically Active Element is selected from the group consisting of Pt, Pd, Au, Ag, Cu, Ni, Fe, Co, Ru and Rh.

15. The electrochemical device of claim 1, wherein the reaction product comprises at least one of CO, $HCO^-$, $H_2CO$, $(HCOO)^-$, HCOOH, $CH_3OH$, $CH_4$, $C_2H_4$, $CH_3CH_2OH$, $CH_3COO^-$, $CH_3COOH$, $C_2H_6$, $(COOH)_2$, $(COO^-)_2$, and $CF_3COOH$.

16. The electrochemical device of claim 15, wherein said reaction product is one of formic acid (HCOOH) and carbon monoxide (CO).

17. The electrochemical device of claim 1, wherein said membrane comprises positively charged amines.

18. The electrochemical device of claim 17, wherein said positively charged amines are imidazoliums or pyridiniums.

* * * * *